(12) United States Patent
Kress

(10) Patent No.: US 12,310,560 B2
(45) Date of Patent: May 27, 2025

(54) ENDOSCOPE WITH QUICK-CHANGE TUBES

(71) Applicant: ES ENDOMED SOLUTIONS GMBH, Essenbach (DE)

(72) Inventor: Jürgen Kress, Essenbach (DE)

(73) Assignee: ES ENDOMED SOLUTIONS GMBH, Essenbach (DE)

( * ) Notice: Subject to any disclaimer, the term of this patent is extended or adjusted under 35 U.S.C. 154(b) by 758 days.

(21) Appl. No.: 17/436,152

(22) PCT Filed: Mar. 11, 2020

(86) PCT No.: PCT/IB2020/000131
§ 371 (c)(1),
(2) Date: Sep. 3, 2021

(87) PCT Pub. No.: WO2020/178634
PCT Pub. Date: Sep. 10, 2020

(65) Prior Publication Data
US 2022/0125283 A1 Apr. 28, 2022

(30) Foreign Application Priority Data
Mar. 4, 2019 (DE) ...................... 10 2019 105 438.9

(51) Int. Cl.
*A61B 1/018* (2006.01)
*A61B 1/00* (2006.01)
*A61B 1/015* (2006.01)

(52) U.S. Cl.
CPC .......... *A61B 1/018* (2013.01); *A61B 1/00068* (2013.01); *A61B 1/00073* (2013.01);
(Continued)

(58) Field of Classification Search
CPC . A61B 1/018; A61B 1/00068; A61B 1/00073; A61B 1/00105; A61B 1/0014;
(Continued)

(56) References Cited

U.S. PATENT DOCUMENTS 4,616,631 A * 10/1986 Takahashi .......... A61B 1/00165
600/920
4,826,280 A * 5/1989 Hiramoto ........... A61B 1/00073
385/116
(Continued)

FOREIGN PATENT DOCUMENTS

DE 102012105370 A1 12/2013
EP 1284120 A1 * 2/2003 .......... A61B 1/00073

*Primary Examiner* — John P Leubecker
*Assistant Examiner* — Li-Ting Song
(74) *Attorney, Agent, or Firm* — DP IP GROUP; Franco S. De Liguori

(57) ABSTRACT

An endoscope for the minimal invasive examination or surgical treatment of a patient has a flexible tubular shaft for insertion into the patient, a grip attached to a proximal end of the shaft for holding the endoscope, and at least one hollow tube. The shaft has at least one groove extending axially along an outer face of the shaft and in which the tube is removably housed. The tube has at least one working channel for guiding a surgical instrument, and/or carrying water or air to or providing suction at the shaft distal end. The shaft groove and the tube are dimensioned relative one another such that at least one free section of the tube is afforded play in the groove. In the straight extended state of the shaft, the at least one free section has an exterior cross-section which is slightly smaller than an interior cross-section of the groove.

19 Claims, 9 Drawing Sheets

(52) U.S. Cl.
CPC ........ *A61B 1/00105* (2013.01); *A61B 1/0014* (2013.01); *A61B 1/00144* (2013.01); *A61B 1/015* (2013.01)

(58) Field of Classification Search
CPC ..... A61B 1/00144; A61B 1/015; A61B 1/012; A61B 1/005; A61B 1/00078
See application file for complete search history.

(56) References Cited

U.S. PATENT DOCUMENTS

| | | | | |
|---|---|---|---|---|
| 4,869,238 | A * | 9/1989 | Opie | A61B 1/00071 600/920 |
| 4,947,827 | A * | 8/1990 | Opie | A61B 1/00073 600/149 |
| 5,630,795 | A * | 5/1997 | Kuramoto | A61B 1/00137 604/35 |
| 5,944,654 | A * | 8/1999 | Crawford | A61B 1/127 600/128 |
| 6,179,776 | B1 * | 1/2001 | Adams | A61B 1/00078 600/146 |
| 9,283,342 | B1 * | 3/2016 | Gardner | A61B 1/267 |
| 2003/0036679 | A1 * | 2/2003 | Kortenbach | A61B 1/00087 600/104 |
| 2003/0171650 | A1 * | 9/2003 | Tartaglia | A61B 1/0053 600/114 |
| 2008/0249357 | A1 * | 10/2008 | Soetermans | A61B 1/00105 600/114 |
| 2014/0005480 | A1 * | 1/2014 | Wagner | A61B 1/005 600/123 |
| 2014/0073854 | A1 * | 3/2014 | Vincent | A61B 1/0014 600/104 |
| 2016/0095510 | A1 * | 4/2016 | Oskin | A61B 1/00073 600/125 |
| 2018/0185007 | A1 * | 7/2018 | Andersen | A61B 1/31 |
| 2022/0192722 | A1 * | 6/2022 | Harshman | A61B 17/3472 |

* cited by examiner

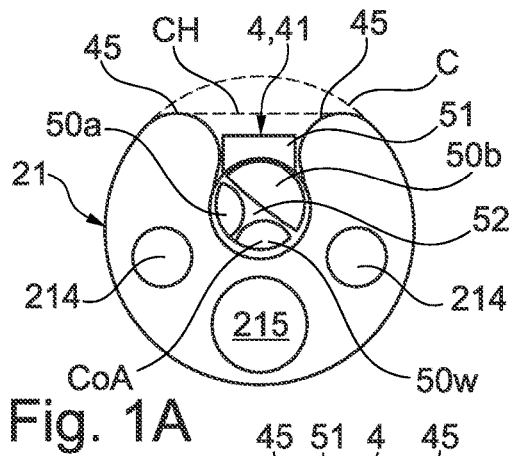
Fig. 1A
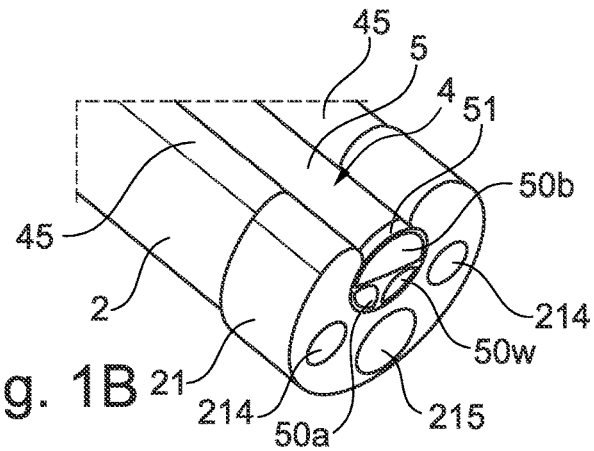
Fig. 1B
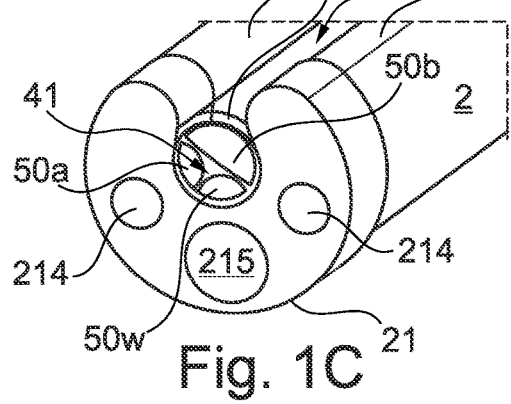
Fig. 1C
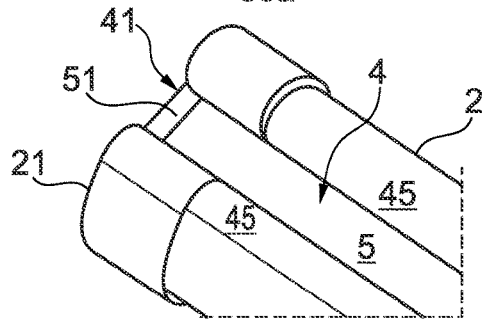
Fig. 1D
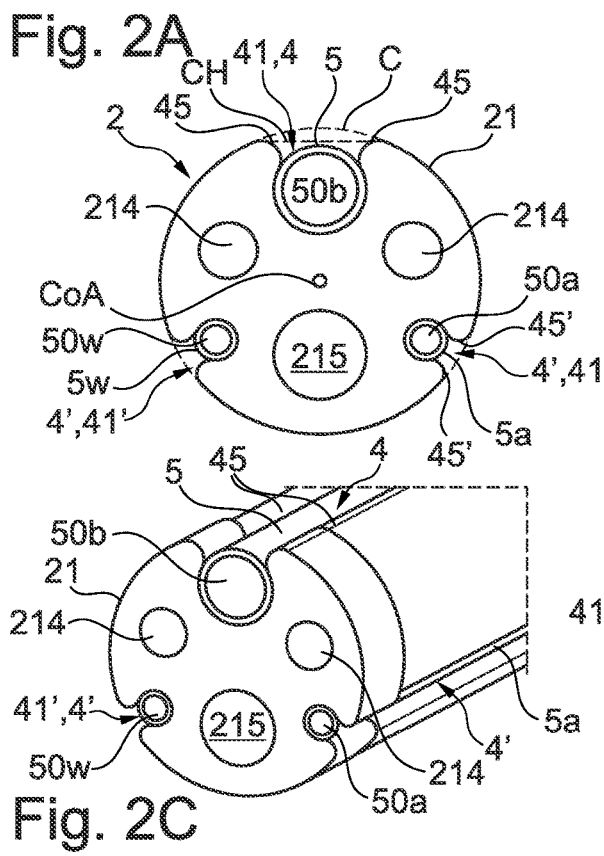
Fig. 2A
Fig. 2C
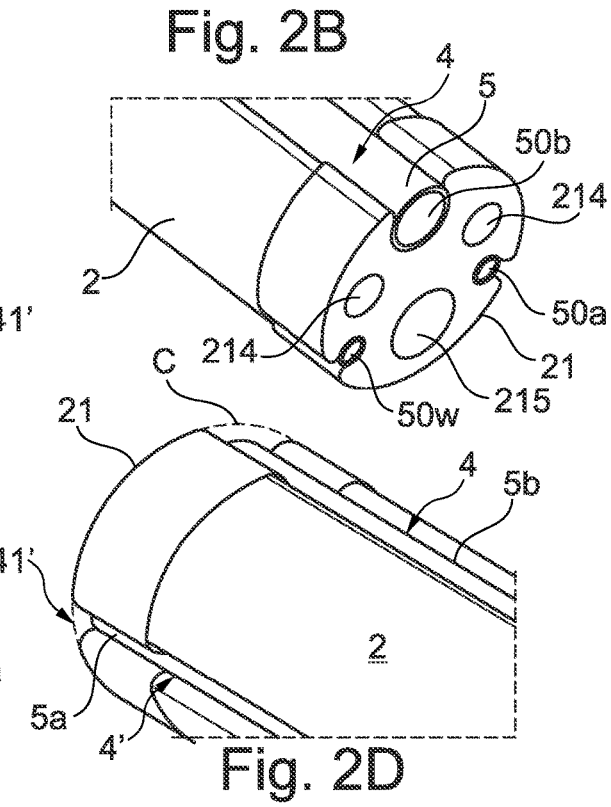
Fig. 2B
Fig. 2D

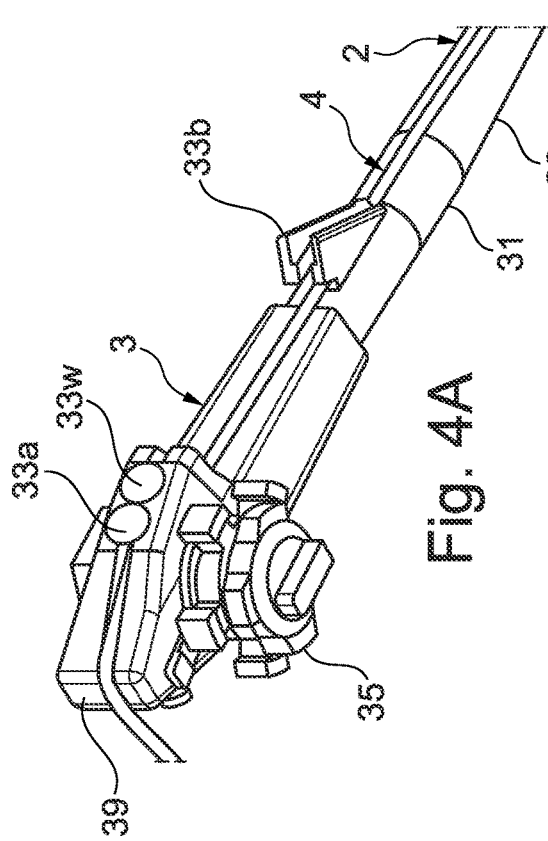
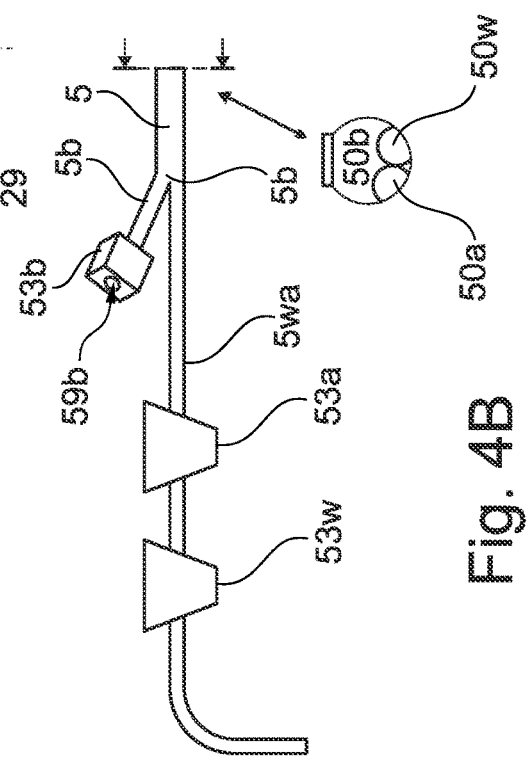
Fig. 3A
Fig. 4A
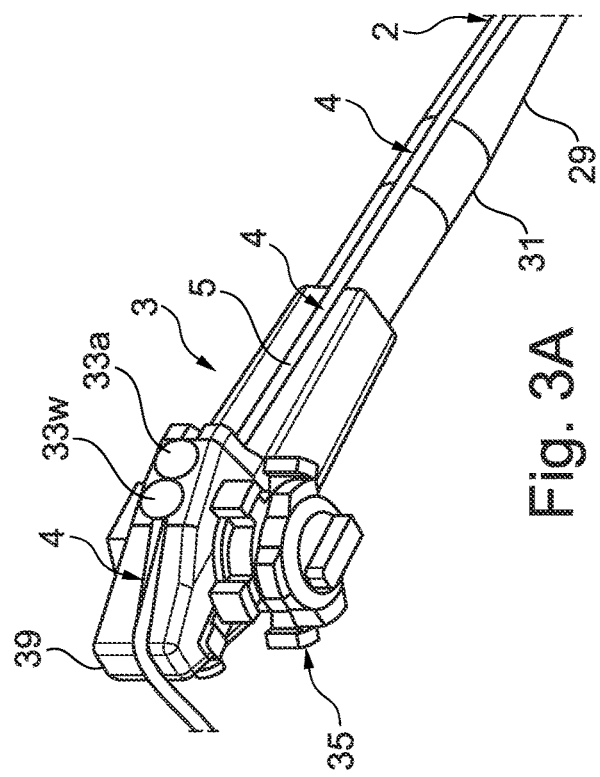
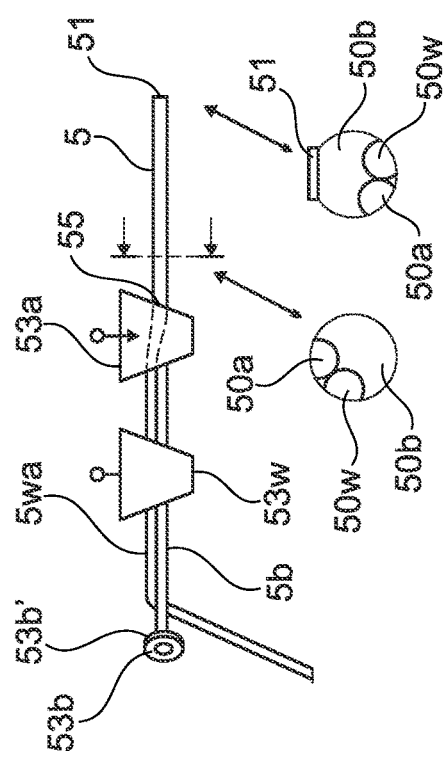
Fig. 3B
Fig. 4B

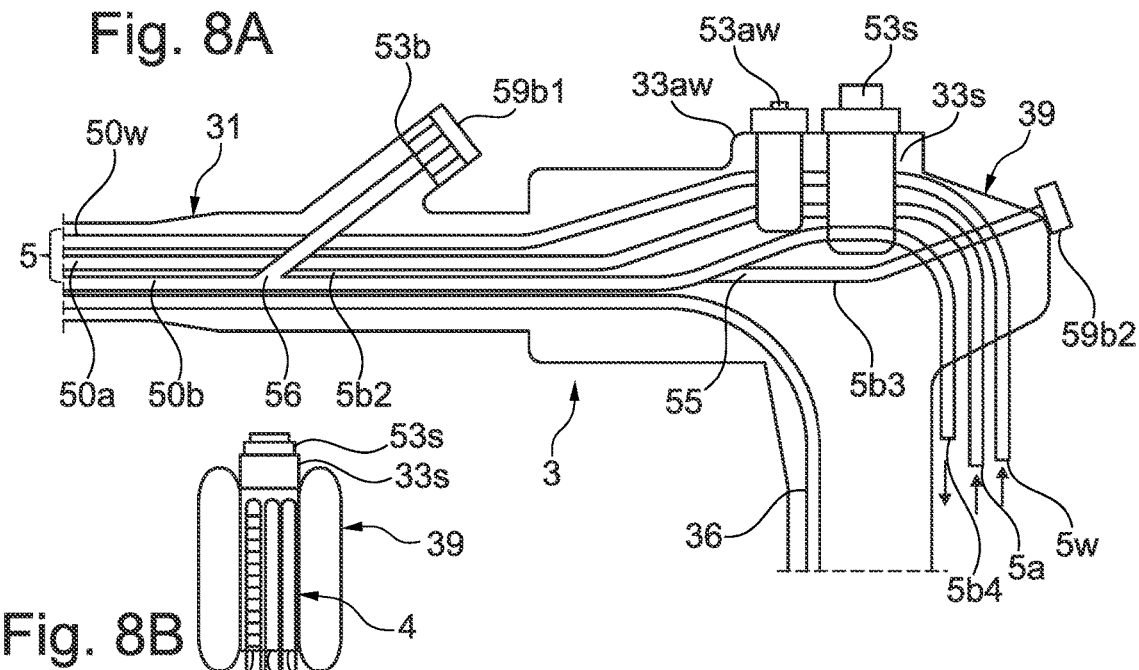
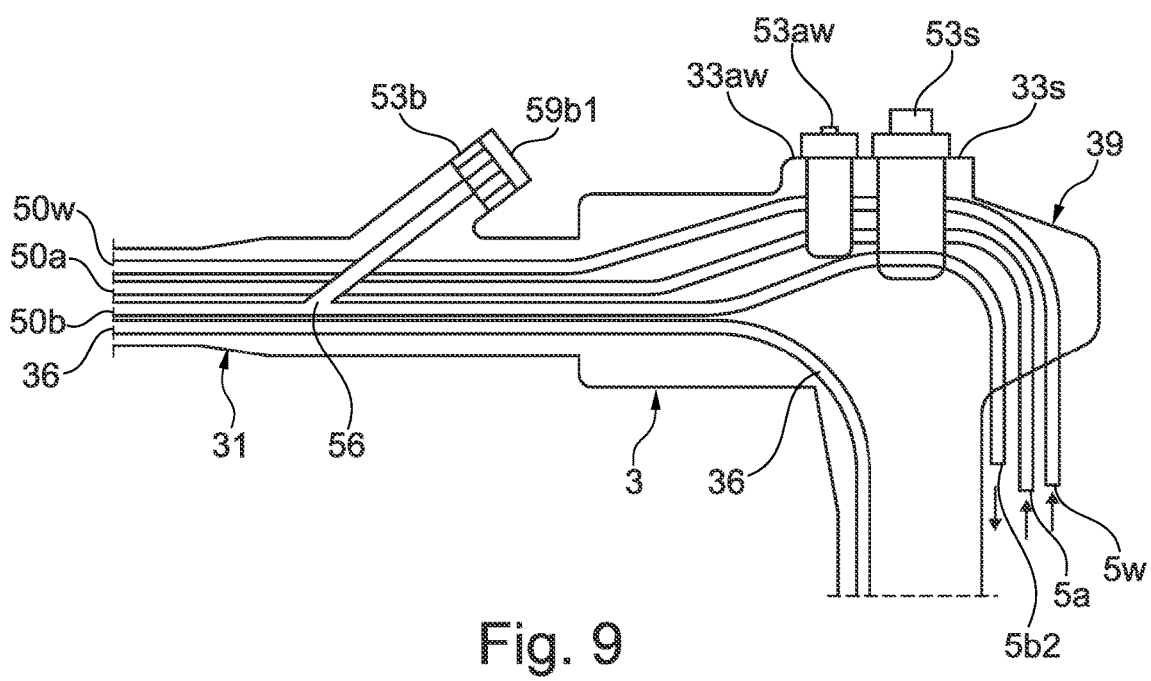

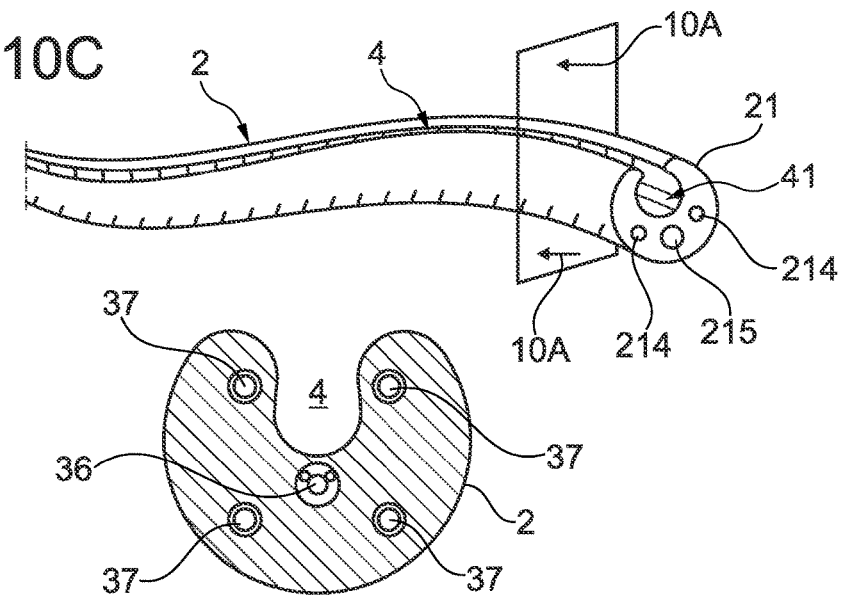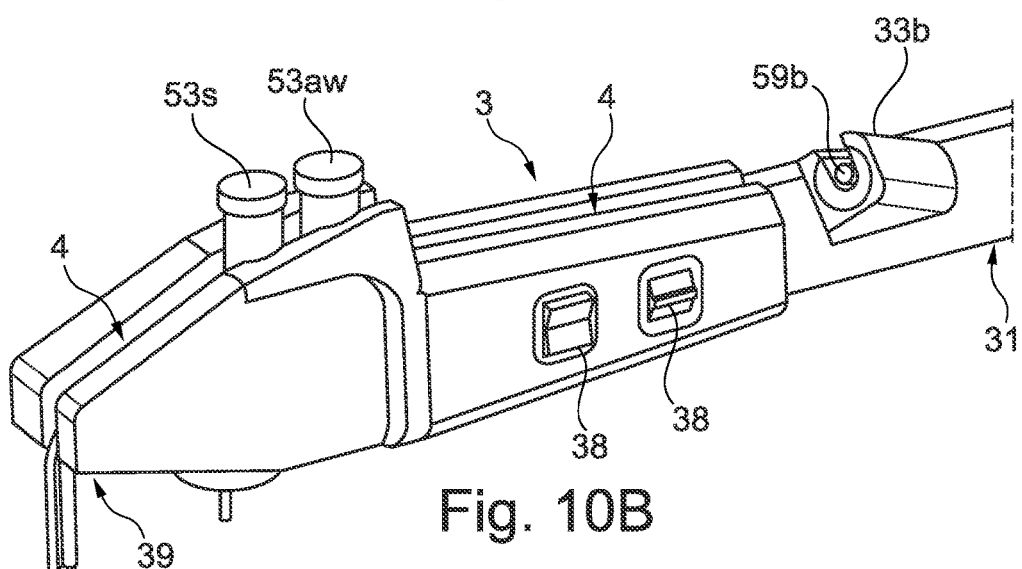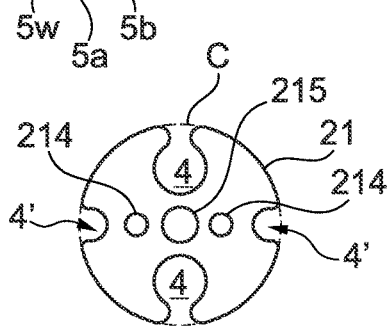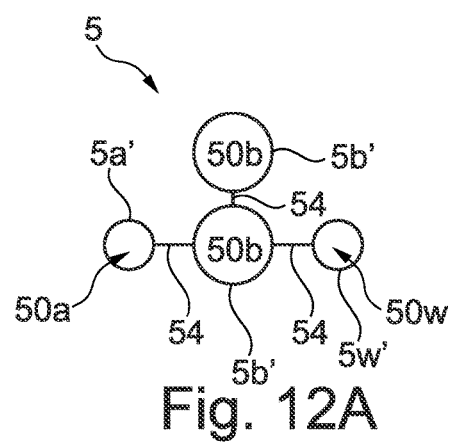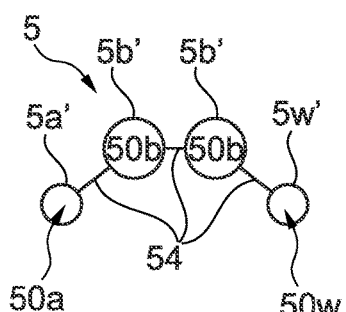

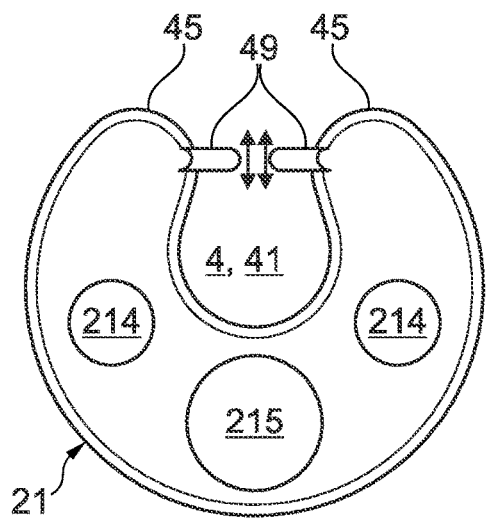
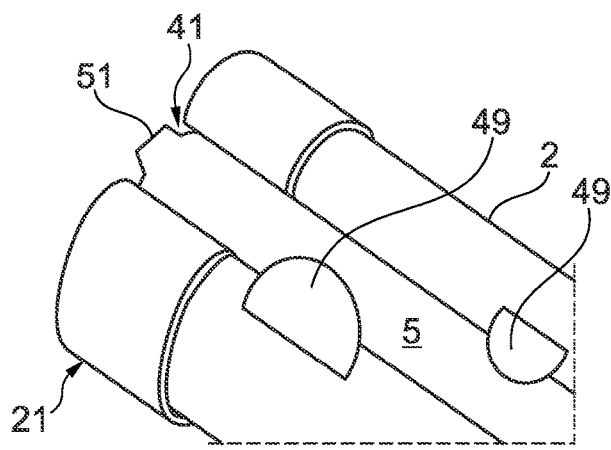
Fig. 14A　　Fig. 14B
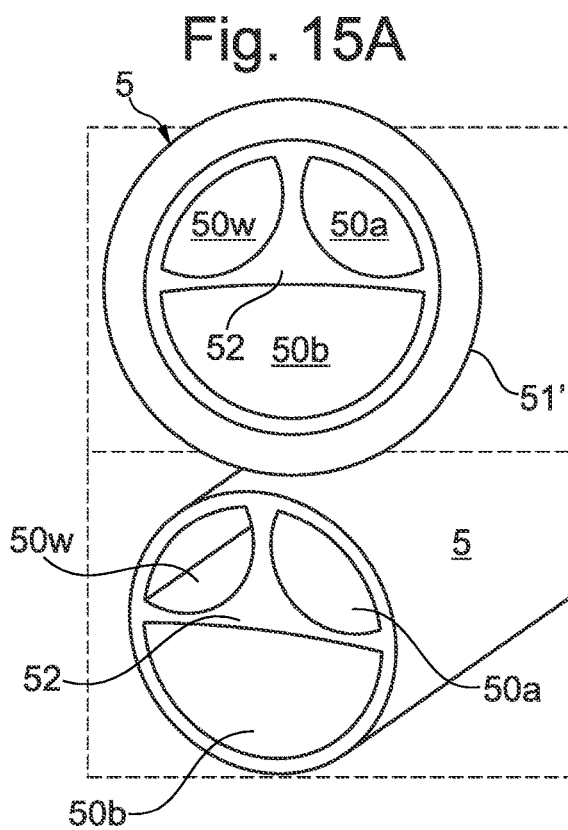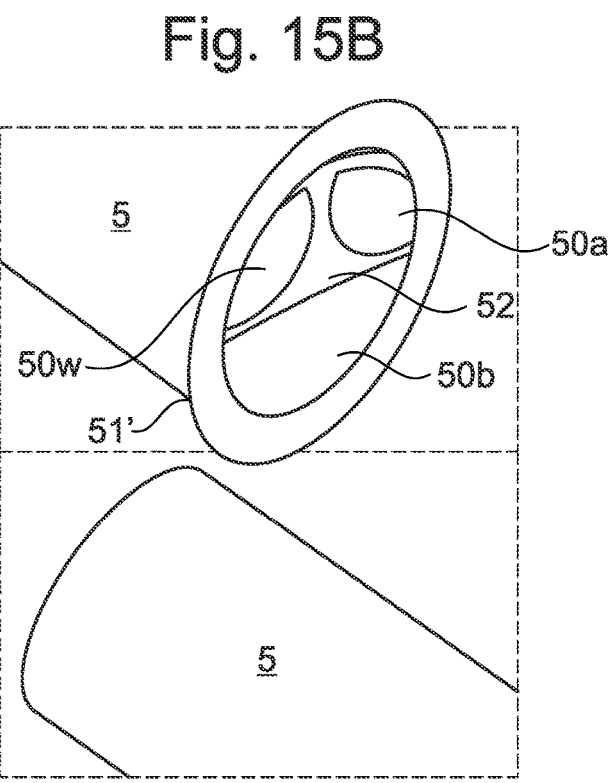

ENDOSCOPE WITH QUICK-CHANGE TUBES

BACKGROUND

Field

This invention relates to endoscopes for minimal invasive examination and surgical procedures of patients, more specifically, to endoscopes with channels for guiding a surgical instrument or carrying water and air during a medical procedure, whereby the endoscopes allow for quick sterilization and reuse. Furthermore, this invention presents procedures for readying such an endoscope for (re-)use before and after an examination or surgical operation.

Background Information

Endoscopes are instruments for performing minimally invasive diagnosis or surgery inside cavities and hollow organs of a patient causing only minimal operational trauma and stress. To this end, an endoscope comprises a holding grip attached to the proximal end of a long, flexible tubular member or shaft for insertion into an orifice or small incision in the skin of the patient. To facilitate the insertion and keep the trauma and pain for the patient as small as possible, the shaft has a smooth outer skin and is designed to have a minimal cross section. Inside it optical fibers run to its distal end for guiding light into and optical information out of the patient, thereby enabling visual diagnosis as well as visual monitoring during surgical procedures. As an alternative to fiber optics there may be used a camera chip integrated into the distal end for observation and a miniature light source, like an LED, for illumination, both being connected by electrical wires running inside the shaft.

During use of the endoscope, the distal end of the shaft is guided to the desired spot inside the patient by bending its distal end in the appropriate direction while slowly inserting/retracting the shaft. This bending of the shaft (near) its distal end can be controlled by mechanical (Bowden) cables or wires running along the sides inside the shaft, these cables being connected to appropriate means, usually control wheels, ergonomically positioned on the grip of the endoscope to facilitate intuitive and easy use of the endoscope. Also known are hydraulically actuated endoscopes, that have an hydraulic system with hydraulic channels integrated into the shaft for moving its distal end and which are controlled by means of switches, for instance rocker switches, positioned in the grip within easy reach.

To allow surgical procedures, like for instance a biopsy, in addition to visual diagnosis, the shaft of known endoscopes usually has an axial instrument channel for guiding inside it a wire-controlled surgical instrument like a forceps, surgical scissors or a sling. This channel may also be put to other uses, such as carrying water and air to or providing suction at the operating spot. However, since it is often desirable to be able to perform all of these simultaneously in order to simplify or even enable certain procedures, further channels may also be present, for instance a separate channel for each function or at least separate channels for the air insufflation and the water cleaning. These channels are then distinguished by their function as working channels for guiding instruments and/or suction of liquids or as supply channels.

The water carried in the water channel may be used to clean the operation spot as well as the instrument or the optical equipment of the endoscope. The air/suction from the, advantageously combined, air/suction channel may, for instance, be used to (temporarily) inflate/deflate cavities or organs around the operation spot, dry it or the instruments or to inflate balloons to keep vessels and cavities dilated for extended periods of time. However, for suctioning off liquids the larger instrument channel is usually used.

Since, without further measures, at least the shaft of an endoscope comes into contact with the bodily fluids of the patient, and may thus be contaminated, a thorough cleaning and sterilization of at least the shaft, but ideally the entire endoscope, is an absolute necessity. However, a sterilization to the necessary degree required is very labour-intensive and time consuming. This is true in particular for endoscopes with channels inside the shaft, as these need to be rinsed out by pumping a disinfectant fluid through them at sufficient pressure and for a certain amount of time. During the sterilization the endoscope is not available for use. From an economic perspective, this is very disadvantageous, as endoscopes are costly pieces of medical equipment, and consequently, to quickly amortize, are desired to be used as often as possible.

To reduce the time spent on preparing an endoscope for reuse between procedures, protective sleeves are known which enclose at least the shaft or extend further to also enclose part or all of the grip. The documents U.S. Pat. No. 5,217,001 and WO 2004/060149 A1 for instance disclose protective covers comprising an at least partially transparent end cap, which is pushed over the distal end of the shaft and a sheath attached to the end cap which from a donut-shaped rolled-up state is unrolled along the shaft to tightly surround the shaft and, possibly, the grip of the endoscope.

A similar endoscope cover is also disclosed in DE 10 2018 110 228, with the difference that a double-layered cover is used, where the additional outer layer, before insertion of the endoscope into the patient, extends beyond the distal end of the shaft and allows attachment to a means keeping the bodily fluid of the patient away from the user of the endoscope, such as a mouthpiece during gastroscopy or a special trouser during colonoscopy, whereby a contamination of the exterior or the user of the endoscope may be prevented effectively.

These protective covers come with hollow tubes attached to the end cap which provide working channels for instruments, water or air/suction as described above. Either, as in the case of DE 10 2018 110 228, they are meant to be inserted as a protective inner cover into an existing channel of the shaft of the endoscope, serving as a barrier between the instrument or the water, air and, in particular, the sucked-in bodily fluids or biological matter and the endoscope, or the tubes are meant to be run along the shaft on its outside as suggested for instance in WO 2004/060149 A1.

In the former case, a disadvantage is that pushing the relatively elastic and soft tubes through the narrow channels in the shaft is a difficult and potentially time consuming step in the preparation of the endoscope. In the latter case, an effective increase in the cross section of the shaft occurs, which potentially increases pain and trauma caused to the patient and thus makes the endoscope less suited for its intended purpose as a minimal invasive instrument.

Furthermore, instrument channels integrated into the shaft of an endoscope have the advantage that they experience only small changes in length when the shaft is flexed and bent, and therefore the forces exerted on the instrument unintentionally by moving the distal end of the shaft using the controls on the grip are also small. If the instrument channel is provided by a tube running along the outside of the shaft, this is no longer the case, making the proper finely actuated handling of a surgical instrument during an operation more difficult.

While in WO 2004/060149 A1 it is proposed to mitigate the increase in cross section by providing grooves for holding the hollow tubes running along the outside of the shaft, yet according to this teaching the tubes are held in the grooves only by the sheath which tightly covers the shaft along with the tubes, thus necessitating use of this sheath. Also, it is not apparent from this document, how the second disadvantage described above might be overcome.

The patent specifications U.S. Pat. No. 7,762,949 B2, U.S. Pat. Nos. 5,944,654, 4,616,631, 6,340,344 B1 and U.S. Pat. No. 4,646,722 each propose endoscopes with shafts having a groove, into which a flexible tube can be inserted. In the document U.S. Pat. No. 6,340,344 B1 the groove is continued along the side of the grip. Only the document shows an embodiment, in which a center of area of a completion of the shaft cross-section to a simple shape lies inside the tube, whereby, however, the tube in its inserted state protrudes beyond this shaft completion, such that the effective shaft cross section is disadvantageously increased. For all embodiments shown therein the tube is retained firmly in the groove along its entire length, such that a relative movement of tube and inner wall of the groove is not possible.

The patent specification U.S. Pat. No. 6,447,445 B1 shows an end cap for the distal end of an endoscope in which flexible tubes providing working channels have fixing structures for securing them against uncontrolled twisting.

The document U.S. Pat. No. 7,311,659 B2 proposes an endoscope shaft with working channels winding spirally around the shaft, which are guided in a common sleeve and not in a groove.

SUMMARY

It is therefore an object of present invention to provide an endoscope with at least one instrument- or biopsy channel respectively in its shaft allowing to carry out surgical procedures including biopsies avoiding the aforedescribed disadvantages. In particular, the endoscope should be easy and quick to clean and sterilize, thereby reducing the time taken to prepare the endoscope for re-use even without employing a protective cover, while at the same time the shaft of the endoscope should not grow in diameter when compared to known endoscopes. Furthermore, the axial position of an instrument deployed in the instrument channel should be affected as little as possible when repositioning the distal end of the shaft. It is a further object, to improve the aforedescribed known endoscopes with changeable tubes in such a way, that an unseating of the tube during bending of the shaft is reliably prevented without making insertion of the tube into the groove significantly more difficult or time consuming.

As solution the present invention proposes a two-part system consisting of an endoscope with a shaft on the outside of which there runs a sufficiently deep, substantially axial groove and a hollow working- and/or supply tube made from a flexible material for providing an instrument- or biopsy channel respectively, a water channel and/or an air/suction channel by means of inserting the tube into the groove in a preparatory step before the operation or examination.

One aspect of present invention achieving these objects is an endoscope which has a working tube removably housed inside a groove running substantially axially along the outside of the shaft from a recess or opening in the distal end at least until some point along the shaft close to its proximal end. The groove may also extend along the entire shaft from its distal end to its proximal end and may even be continued seamlessly in the grip attached to the proximal end of the shaft.

According to the invention, there is at least one section along the common course of the tube and the groove, in which both are shaped in such a way relative to one another, that the tube has play inside the groove, such that it may slightly shift relative to the interior walls of the groove in particular axially but also in regards to a rotation of the tube around the (local) longitudinal axis of the groove.

Such a free section of the tube, of which there may also be several, allows a better adaption to length changes of the groove caused by bending of the shaft, which invariably occur during employment of the endoscope.

The play between tube and groove (interior wall) in the respectively one of the free section/s may in particular be achieved by sizing the cross section of the tube slightly smaller than the cross section of the groove, at least in a state where the shaft is extended straight. For a tube with round cross section this is synonymous to an outer diameter that is smaller than an inner diameter of an at least partially complementarily shaped, such as a U- or Ω-shaped, groove.

If present, the tube sections lying between its free sections are in contrast seated in the groove more firmly, either pressed in exploiting the elasticity of the tube or, alternatively or in addition, glued in with an adhesive of low adhesive strength.

To avoid enlarging the cross-section of the shaft, the shapes and relative sizes of the cross-sections of the hollow tube and the groove are such, that the geometric convex hull of the shaft or at least the completion of the shaft is the same whether the hollow tube is inserted or not. In other words, the tube, when properly housed in the groove on the outside of the shaft, e.g., by pushing or plugging it into the groove as far or deeply as possible, without unduly deforming the, usually elastic, tube from its natural shape, should nowhere extend beyond the convex hull of the shaft.

The term 'convex hull' here is understood in its usual mathematical-geometrical meaning as the smallest convex volume completely containing a certain object.

"Completion" is to be understood here as the imagined completion of the cross section to the, in terms of area, smallest fundamental geometric shape which contains the cross section, wherein in this context ellipses (including circles), regular polygons (including squares) and all shapes, which may be obtained from a regular polygon by compression or stretching along one axis (this comprises rectangles), are viewed as fundamental geometric shapes.

To facilitate fast and easy cleaning and sterilization of the endoscope, sharp inner edges in the groove are to be avoided. The inside of the groove should thus at no point have a curvature radius much smaller than a curvature radius of the cross-section of the hollow tube seated or housed inside it, in particular no smaller than 0.1 mm, ideally no smaller than 0.5 mm.

If the groove is intended to house a tube large enough to serve as instrument channel, it may be arranged and sized in a way to ensure that the axial position of an instrument in the channel relative to the shaft, or more precisely relative to the distal end thereof, changes as little as possible upon flexing and bending of the shaft. To that end, the groove should, along substantially its entire extent, come close to or, ideally, contain a line of vanishing stretch/compression of the shaft, i.e. a line extending axially along the tubular shaft, where the material of the shaft is neither stretched nor compressed when it is subjected to flexing or bending during the insertion into the patient, for instance due to the user of the endoscope operating the control wires controlling the (bending of the) distal end of the shaft.

This can, for instance, be achieved by making the groove deep enough—referring to its radial extent—to come close to or contain the center of area of either the (actual) cross-section of the shaft or the (virtual) completion of that cross section to the, by area, smallest basic geometric shape containing it. The groove can be considered close to the center of area of some cross section of the shaft, if the distance between the two, in that cross-section is equal to or less than half the radius of the smallest circle containing that cross-section. As basic geometric shapes are considered in this context ellipses (including circles), regular polygons (including squares) and all shapes obtainable by compressing a regular polygon along one axis (this includes rectangles). A common completing shape of a cross-section of a shaft according to this invention is a circle or an ellipse close to a circle, i.e. one having a small eccentricity. The center of area of that completing shape is then the center of that circle or ellipse.

Another aspect of present invention is a hollow tube made from a flexible material for providing at least a biopsy or instrument channel to an endoscope having a groove running along the outside of its shaft. The tube has a proximal end, in which there is a least an opening for inserting a surgical instrument, such as a biopsy forceps, attached to one end of a guiding and controlling wire, and a distal end, with which it is to be positioned in a recess in the distal end of shaft of an endoscope according to this invention. In the distal end of the tube there is at least one opening from which the wire-guided surgical instrument can issue to reach the desired operating spot inside the patient. The tube may also comprise one or several branching points and thereby have more than one proximal end.

The tube is made from flexible material, such that it may bend along with the shaft and does not hinder the repositioning, in particular of the distal end, thereof. If a material such as synthetic rubber or PET is used, which at low manufacturing cost can be brought into almost any shape, it becomes economically feasible to regard the hollow tube according to the invention as a disposable, single-use product. Not having to clean and sterilize the tube after use can dramatically speed up the times required to prepare an endoscope according to the invention for use or re-use.

The tube may have a circular, elliptical or oval cross-section which is either of the same size or slightly larger than that of the groove. The tube may consist of a single part but it may also have two or more, in particular three sub-tubes running parallel to each other, with each sub-tube having a circular, elliptical or, in general, oval cross-section and being connected to each other either directly or via thin bridges made of the same material as the tube.

Using a tube of non-circular cross-section or one that consists of more than one part, when it is housed or seated in a non-circular groove with similar or substantially matching cross-section, has the advantage that its angular orientation relative to the shaft is substantially fixed and cannot change during operation of the endoscope, in particular during insertion or repositioning of the shaft involving frequent bending of the shaft and its distal end into different directions.

In addition or alternatively to sub-tubes, the tube proposed by this invention may also have internal walls subdividing the hollow inside of the tube into two or more, in particular three, channels, running essentially parallel to each other in axial direction through the tube.

The hollow inside of the tube must be wide enough to allow passage for an instrument attached to a guiding and controlling wire. In particular, it should be at least about 1 mm wide, better 2.5 mm to 3.6 mm wide, but no wider than about 5 mm. An instrument tube thus has to have a much larger interior diameter and larger interior cross-sectional area respectively, than a supply tube for supplying water and/or air/suction at the operation spot.

The working and/or supply tube according to the invention, in particular a comparatively thicker instrument tube, can have rubber-gaiter-like or spiral-tube-like sections or be shaped entirely bellows-like or spiral-tube-like in order to, as for a straw, improve its flexibility and to ensure a good length compensation to the bending and twisting of the shaft during its use.

The walls of the tube, including any internal subdividing walls, should be as thin as possible while ensuring that the tube does not easily rupture or break during its intended use, in particular when inserting or plugging the tube into a groove of the shaft of an endoscope according to this invention or when inserting an instrument into the hollow tube.

Before installation of the tube in the groove of the shaft of an endoscope according to the invention, an end cap may first be pushed over the distal end of the tube. The end cap has the function of securely holding the distal end of the tube in the recess or opening of the distal end of the shaft. Alternatively or additionally, the distal end of the tube may have a slightly larger cross-section than the rest of the tube, in order to increase the elastic clamping forces holding it in place after installation.

Preparing an endoscope according to this invention for use involves essentially only installing the flexible hollow tube in the groove of the shaft and thus is much less time consuming than installing a known endoscope protective cover.

One way of installing the tube is by placing it on top of the groove such that its distal end is flush with the distal end of the shaft, remembering to first install an end cap if necessary, and then pushing it into the groove, starting at the distal end and working upwards along the shaft towards the proximal end until the tube is securely seated inside the groove along its full extent. Finally, the proximal end of the instrument channel of the tube is secured by appropriate means to the grip of the endoscope, for instance by placing a fixing structure of the proximal end of the tube inside a mounting bracket provided for this purpose on the grip. Similarly, the proximal ends of any water- or air/suction channels of the tube are connected to the appropriate places, e.g. valves controlling the flow of water or air, in particular valves mounted in mounting brackets provided for them on the grip of the endoscope, or to outlets of an apparatus providing such controlled flow of water or air.

If the instrument channel is used as combined suction channel, a continuation branching of from the main channel has to be connected to a vacuum source. A control valve is preferable situated in this continuation, which is inserted into an, ideally ergonomically positioned, seat or fixture of the grip, in order that a user of the endoscope according to the invention may control a suction procedure without having to take his hands off the grip.

If the water or air/suction channels are provided by separate hollow tubes, these can be installed separate grooves in the outside of the shaft, if provided, or they are installed together with the instrument channel tube in a single groove of appropriate diameter/cross-section.

Preparation of an endoscope according to this invention for re-use between operations on the same or different patients involves the steps of removing the one or more tubes housed in the one or more grooves, e.g., by pulling them out of their seat in the groove starting from their respective proximal ends. The tube or tubes is/are then either cleaned and sterilized separately from the endoscope or, preferably, disposed of. The endoscope is washed and sterilized to ensure any contaminating matter and any microbes and germs are removed or neutralized. This is facilitated by the geometric design of the groove without sharp inner and preferably also outer edges. After sterilization the endoscope is set-up for use by installing a new working tube as described above.

The distinguishing feature of the proposed system consisting of an endoscope with a grooved shaft and a tube detachably inserted therein is that all internal channel systems that carry liquids or come into contact with liquids are dispensed with and that these are relocated to the outside where they are easily accessible for cleaning and sterilization. Even so, an enlargement of the shaft cross-section is advantageously avoided and the effects of elongation and kinking on the axial position of instruments located in the working channel are minimized.

The great advantage of the system according to the invention is that there are no longer any channels that are necessary in the hermetically sealed interior of the endoscope or rather its shaft. This increases, on the one hand, the speed of, but even more so improves the hygienic safety in cleaning and sterilization. There are no longer any spaces that are difficult to reach and clean for germs such as hidden tubes, corners, connections, curves, tube surface grooves on the inside of the working channel. Through this the endoscope according to the invention can also be used with an exchangeable working tube without a protective cover, which enables a considerable reduction in the time between two successive examinations with uncompromised contamination protection.

In the following, preferred embodiments of the invention will be described, which may be realized alone or in combination, as long as they do not obviously contradict each other.

In some embodiments there is only a single free section. This free section is then preferably located at the transition between the endoscope's grip and its shaft or approximately in the middle of the shaft and has a preferred length of between 5%-50%, particularly preferred a length of between 10%-20% of the shaft length.

Alternatively other embodiments of the endoscope according to the invention have multiple free sections, which are preferably evenly distributed along the shaft and each have a length of preferably between 2% and 20%, particularly preferably between 5% and 10% of the shaft length. The free section closest to the distal end of the shaft is preferably space from this end by a distance equal to its length.

In the free sections the tube preferably has, in comparison to the remaining sections, an increased flexibility, by means of which it can adapt more readily to deformations of the groove, in particular (local) stretching or compression or twisting. This may be achieved by the elastic tube having a lower wall thickness there. Alternatively or additionally, a different material with a higher elasticity (lower Young modulus) may be used.

Another, alternatively or additionally usable solution for greater deformability is to fashion the tube in the free sections like a rubber gaiter or bellows so that it can easily stretch/compress by a factor of 2-3 in the axial direction, as is known, for example, from a curved cocktail straw. Instead of or in combination with a bellows-like design, a spiral-tube-like design can also be selected. The difference is that a bellows has several consecutive, non-contiguous circular constrictions or thickenings, while a spiral tube is characterized by a contiguous constriction or thickening that encircles the tube in a helical manner.

In yet other embodiments, the length of the free area is 100% of the shaft length or, alternatively, also the length of the groove, if this is also continued in the grip. This means that the tube has play over the entire length of the shaft or the groove and can easily move with respect to the walls of the groove. In these configurations, however, it can become a problem that the tube easily jumps out of the groove due to the play when the shaft is bent and rotated. If this occurs during an examination, the endoscope would have to be pulled out again and the tube reinserted correctly. This can be countered by using an Ω-shaped groove with a large diameter-to-neck ratio of 2:1 or more.

So that inserting or pressing the tube, which should remain easily exchangeable, is not made too difficult, it is recommended to vary the diameter-to-neck ratio in the course of the groove and to use a large to very large one to secure the tube only in some sections.

Alternatively or additionally, elastic retaining wings projecting into the groove or the groove neck can also be provided. Due to its elasticity, the tube can be pressed in or pulled out with comparatively little pressure. It becomes active while using the endoscope. The endoscope is held securely in the groove by the retaining wings. The advantage of the retaining wings is that a groove with a constant cross section can be made in the shaft, which is easier to manufacture than the previously described groove with a varying cross section.

In order to prevent the distal end of the tube from sliding back into the groove as the length of groove unavoidably changes, it is proposed to provide an anti-slip safety. This can take the form of a disk or a collar partially encircling the distal end of the tube.

The shaft of the endoscope according to the invention may have only a single groove or it may have two or more grooves of the same or different lengths, cross-sectional shapes and areas. In some embodiments of the endoscope of this invention, the shaft has three grooves, where one may be larger, in particular it may have a larger cross-sectional area, than the other two and may serve to house a flexible hollow tube providing an instrument channel.

In preferred embodiments of the endoscope, the groove for housing the hollow tube runs from the distal end of the shaft all the way to the proximal end of the shaft. In further preferred embodiments, the groove is continued seamlessly in the grip, running preferably along the upper side of the grip.

Although it is not as critical, to further enhance ease of cleaning and sterilization, and moreover to prevent damage to the comparatively thin-walled hollow tubes when installing them in the groove, sharp outer edges at the radially outward upper end of the groove may also be avoided in some preferred embodiments of this invention.

The cross-section of the groove or grooves in the shaft may be U-shaped, thus allowing better access during cleaning of the endoscope. Alternatively, or additionally, some or all sections of the groove may be Ω-shaped in order to enhance retention of the tube in the groove especially during movement, flexing and bending of the shaft.

The bulge-neck ratio, i.e. the ratio between the largest and smallest width of an Ω-shaped groove, should not be too much greater than 1.0 (which corresponds to a U-shaped cross-section), so as not to make plugging or pressing the tube into its seat in the groove too difficult and potentially damaging for the tube. Also, the larger the bulge-neck ratio the harder the inside of the groove is accessible for cleaning. Thus the bulge-neck ratio of an Ω-shaped groove according to this invention should preferably not be greater than 2.0 and ideally lie between about 1.1 and 1.5.

In some embodiments the groove has a larger bulge-neck-ratio outside the free sections than inside them. In particular the bulge-neck-ratio may there attain a value of 2.0 or higher, in order to ensure fixation of the tube, which is movable relative to the groove inside the free sections, outside of the free sections.

In some embodiments of the endoscope of this invention the groove may have a cross-section which changes along its extent. It may change in that a diameter or width of the groove changes, in particular being smaller at or near the distal end of the shaft as well as preferably at least on further region close to or at the proximal end of the groove. Alternatively or additionally it may change in that the cross section varies between different shapes, for instance being Ω-shaped in some sections of the groove and U-shaped in others. In preferable embodiments the groove has for instance at least two sections where it is Ω-shaped, one of them being at or near the distal end of the shaft, the other close to the proximal end of the groove, while in the other sections it is U-shaped. Thus the advantage of better retention under movement of the Ω-shaped cross-section is combined with the improved access for cleaning of the U-shaped cross section.

An optimization towards better retention can be achieved by using more and/or longer Ω-shaped sections, an optimization towards better cleanability by using fewer and/or shorter Ω-shaped sections. A good compromise appears to be achieved by using between two and five Ω-Shaped sections each with a length between 2 mm and 20 mm.

Preferably, the cross-section of tube and groove, or, for substantially circular tubes and at least sectionally circular grooves, their diameters should be of similar size, such that the outer side of the tube, when seated in the groove, is flush with the outer side of the shaft. Thus, mathematically speaking, the tube should preferably touch the convex hull or the completion of the shaft. In this way the outside of the shaft with the tube inserted in it is as smooth as possible, facilitating insertion of the endoscope and causing as little pain to the patient as possible. Furthermore, this makes it harder for bodily fluids and the contaminants contained therein to enter into the spaces between tube and groove.

To enhance this effect even further, it is even more preferred by the invention, if the hollow tube has a cross-section matching that of the groove as closely as possible in shape and size. In particular the cross-section of the tube should be thus, that when it is fully inserted in the groove, the outer shape of the shaft with the tube is, within tolerances, equal to the convex hull or the completion of the shaft as defined above.

A preferred embodiment of the tube for use with an endoscope having a groove in its shaft for housing a hollow tube according to this invention has a circular cross-section with internal walls subdividing the interior of the tube into two or three channels. One larger channel serving as passage for surgical instruments (instrument channel), and one or two smaller channels of equal or similar diameter serving to carry water and/or air (water and air/suction channels).

In some embodiments of the invention with a two or three-channel tube the instrument channel branches away in a Y-junction from the other two channels, being continued as a separate instrument tube running at an angle to the axial direction of the shaft to where its proximal end is secured to the grip, while the other (two) channel(s) continue from the Y-junction as a second separate tube. This second separate tube may be housed in the groove and may continue to follow the axial direction of the shaft.

In other embodiments of the invention with a two or three-channel tube, it is the water and/or air/suction channel(s) that branch of from the instrument channel, which continues straight and remains housed in the groove until its proximal end. In these embodiments it is preferable if the groove is continued seamlessly in the grip extending to a proximal end thereof, where, preferably a means for securing the proximal end of the instrument channel is provided. The water and/or air channels branching off part of the way along the groove, such as in the area of the distal end of the grip or the proximal end of the shaft, are preferably led to mounting brackets for valves controlling the flow of water and/or air in the water and air/suction channel respectively.

To allow water carried in the water channel to clean the optics contained in the distal end of the shaft, the angular alignment of the tube at the distal end should be such, that the outlet of the water channel is as close to these optics as possible. Usually, this means the water channel outlet needs to be radially closer to a center of area of the distal end than the other two outlets of the air/suction and instrument channel respectively and thus it needs to be further from the upper opening of the groove. However, in the embodiments of the invention with a multi-channel tube, where the water and/or air channel branch of from instrument channel, which continues straight along the groove, the direction of this branch-off is directed preferably radially upwards or tangentially to a side, e.g. towards the side where the valve(s) for controlling the flow of air and/or water are mounted. In order to facilitate this without compromising the proper and secure seating of the tube inside the groove around the branching point, this invention proposes that the channels inside the multi-channel tube between its distal end and the branching point twist around each other by some finite angle, in particular an angle between 0 and 180 degrees, preferably between 20 and 90 degrees, even more preferably between 30 and 60 degrees.

Alternatively or additionally, one may use a tube without a twist, or with a smaller twist angle in an embodiment of the endoscope, where the groove, at least between its distal end and a branching-off point of the tube, describes a spiral course on the outside of the shaft in particular a spiral covering an angle of between 0 and 180 degrees, preferably between 20 and 90 degrees, even more preferably between 30 and 60 degrees.

In these embodiments of the endoscope the intended branching-point may be marked by a narrowing or reduction in cross-section of the groove, as from that point on only the instrument tube needs to be housed in it, which has a smaller diameter/cross-sectional area as the full multi-channel tube as it is housed in the groove between the branching point and the distal end of the shaft.

In order to ensure that alignment does not change during movement of the shaft also in the case that the tube has a circular cross-section, it is proposed to equip it with fixing lug, i.e., a radial protrusion, at least at or near a distal end of the tube, but preferably also at a second location along its extend. The fixing lug or lugs should have a width equal to that of the groove at the point where the lug comes to lie when the tube is housed in the groove of an endoscope according to the invention. If, in particular an endoscope with a Ω- or U-shaped groove is used, i.e. a groove with a partially circular cross-section with or without a neck at an upper, radially outward side, the width of the fixing lug should be equal to that of the opening of the groove (U-shaped groove) or the neck (Ω-shaped groove).

In alternative preferred embodiments of the system according to the invention comprising an endoscope and exchangeable tube, the latter consists of several, in particular three or four, parallel partial or sub-tubes, which are connected to each other by thin bridges. The bridges preferably consist of the same (plastic) material as the sub-tubes, and are integral, i.e. form one piece with them. The advantage of this embodiment is that no branches need to be provided at precisely defined points, since the sub-tubes can be separated from one another simply by cutting through the bridges at any point or in any area. This enormously facilitates the use in endoscopes with different lengths (shaft length, grip length, distance from the endoscope tip to the junction points of the sub-tubes) without the preparation time of the endoscope being measurably increased before use.

Embodiments with three or four sub-tubes are particularly preferred. An embodiment with three sub-tubes comprises, for example, a central sub-tube with a sufficiently large diameter so that it can serve as an instrument tube. With this central instrument part tube there are two sides running, preferably symmetrically arranged, sub-tube with a smaller diameter are connected by thin material bridges, i.e. at most about the wall thickness of the sub-tubes. The smaller sub-tubes are used here to provide (compressed) air and a water channel.

In a modification of this embodiment, the instrument channel sub-tube can also be doubled so that there are two parallel instrument channels which can be arranged one above the other or side-by-side. This allows to simultaneously introduce and work with two instruments, which in some situations accelerates an operation or even makes it possible in the first place.

For the endoscope to be properly usable during an operation, the proximal ends of the different channels, instrument, water and air/suction, have to be secured or connected appropriately. The proximal end of the instrument channel needs to be secured to the grip of the endoscope, while the proximal ends of the water and air/suction channel need to be connected to a source of a controlled flow of water and air (provided at an over- or under-pressure).

A simple way to securing the proximal end of the instrument channel would be to tie it to the grip using a wire or cord. This, however, is neither very secure nor fast to do. It is therefore proposed by this invention to fashion the proximal end of the instrument channel as a securing or fixing structure such as an oblong or disc-shaped block and to provide a retaining recess for inserting this securing structure on the grip, preferably upon its upper side to facilitate access to the proximal end. The retaining recess should have a hollow inside with a complementarily shape to that of the fixing structure and must allow insertion of the fixing structure, e.g., by being open on one side. In particular, the retaining recess may consist of two opposing U-shaped rails oriented parallel to each other, into which the fixing structure, in particular the oblong or disc-like block, may be slid from above. A taper either in the distance between the rails or in the width of each rail or, alternatively or additionally, the oblong or disc block or both ensures a progressive increase in the elastic clamping force holding the fixing structure in place.

Alternatively or in addition, the upper end of the securing structure may have a step or other enlargement in its extent along the axial direction of the tube, which serves to provide a larger clamping force. Other methods of securely holding the fixing structure will occur to the skilled person.

Controllability of a water and/or air by the user of the endoscope can be achieved by having valves within easy reach of his hands during operation, in particular valves installed in mounting brackets provided for them on the grip of the endoscope. These valves may be separate parts to which the proximal end of the hollow tube have to be connected during preparation of the endoscope. Alternatively, to further reduce preparation time, this invention proposes to integrate the valves into the tube, i.e. have them pre-installed in the tube. To facilitate their fastening on the grip, it is further suggested to encase the valves at least partially in valve blocks, for instance valve blocks made from the same material as the tube, of oblong or cylindrical shape, which during set-up of the endoscope may be quickly slid into appropriately shaped recesses on the grip.

The cross-section of the shaft of an endoscope according to the invention may in preferred embodiments be at least substantially mirror symmetric over its whole length. In particular it may be circular, elliptical or oval. In these embodiments, in order to ensure that it lies close to a line of vanishing or minimal stretch/compression of the shaft during bending, a groove housing a tube comprising an instrument channel may lie in a plane of symmetry of the shaft.

In preferred embodiments of the endoscope of the present invention, the shaft is not designed as a plastic-encased metallic spiral spring, as is customary in the prior art, but is made of solid material. In particular when using a fully plastic shaft, this has the great advantage that a better compromise can be found between rigidity on the one hand and flexibility on the other through the choice of material. A certain rigidity is necessary in order to ensure the directional controllability of the endoscope tip when it is inserted into the body under the influence of the deflecting resistance of tissue and organs. On the other hand, the rigidity must of course not be so high that there is a risk of injury. In the case of the usual endoscope shafts with a spiral spring as the shaping structure, however, the rigidity is quite low, which makes it difficult to reach the desired surgical or examination site in the patient.

The use of a solid material shaft in connection with an endoscope equipped with working channels is only possible within the scope of the present invention, because the working channels of a solid material shaft would become damaged and unusable over time due to material fatigue. Through the present advantageously proposed endoscope with externally accessible, removable working channels, this limitation is overcome, since the working channels and the tubes providing them after each use of the endoscope must be changed.

However, a solid material shaft can hardly be combined with a control by means of an internal Bowden cable system. It is therefore proposed to insert, or, depending on the manufacturing process of the shaft, to cast in hydraulic lines of a hydraulic control in the solid material. The operation, i.e., the control of the hydraulic pressure applied to the individual lines, would be carried out by the user in a basically known manner by means of rocker switches embedded in the grip in an ergonomically favorable position instead of the rotary wheels customary in Bowden cable controls. Lighting and optical monitoring could still be implemented either by means of optical fibers or electrically controlled elements (cameras, LEDs).

Alternatively or additionally to ensuring retention of the tube inside the groove of an endoscope according to this invention purely by elastic forces, as in the case of a U-shaped groove with a tube of larger width, or a combination of elastic forces and/or geometric constriction, as in the case of an at least partially or sectionally O-shaped groove, a weak and easily removable glue may be used. It may be applied at the time of installation of the tube in the groove during preparation of the endoscope or it may be pre-applied during manufacture of the tube in one or a small number of spots or everywhere along that part of the surface of the tube that is going to come in contact with the inside of the groove.

In further preferred embodiments of the endoscope according to the invention, a contamination protection cover or sleeve is provided which further facilitates the cleaning of the endoscope after use. In a simple embodiment, a known protective cover is pulled over the endoscope shaft before the tube according to the invention is inserted. Such protective sleeves are usually made of a highly elastic material such as latex or nitrile rubber and therefore, before the tube is inserted, assume a cross-section which almost corresponds to the convex hull of the shaft. The tube according to the invention is now inserted into the groove as described above, whereby the sleeve is pressed into the groove and clamped between the outer surface of the tube and the inner wall of the groove. This clamping is stronger, i.e., more powerful, in the areas in which the tube is firmly seated in the groove and weaker in the free areas of the tube according to the invention.

In a modification, a second, outer protective sleeve can be pushed over the inner sleeve and the tube. In this way, contamination protection can be implemented not only for the endoscope itself, but also for the operator if the outer cover is appropriately expanded at the proximal end and fastened in such a way that the operator does not come into contact with body fluids adhering to the endoscope after pulling it out.

In a particularly preferred embodiment, a protective cover is used in which the tube is already integrated into the cover. When pulling on the sleeve, which is preferably done in such a way that the toroidally rolled-up sleeve is placed on the shaft tip and then rolled out along the shaft like a condom, the tube is pressed into the groove at the same time. This allows the sleeve and tube to be installed at the same time, which further advantageously reduces the preparation time for an examination.

In order not to obstruct the optics of the endoscope, a window made of a transparent material is integrated in the tip of the cover. Alternatively, the entire cover tip can also be made of a transparent material. Since the cover does not have to be stretched so much in the area of the tip, a significantly less elastic material can be used than for the rest of the cover.

BRIEF DESCRIPTION OF THE DRAWINGS

There follows a brief description of the drawings:

FIGS. 1A-1D: Multiple views of the distal end of the shaft of a first preferred embodiment of an endoscope according to the invention with a single deep Ω-shaped groove housing three-channel tube.

FIGS. 2A-2D: Multiple views of the distal end of the shaft of a second preferred embodiment of an endoscope according to the invention with three separate grooves, one of which is a deep, mildly Ω-shaped groove housing an instrument channel tube, the other two being smaller and housing a water and air channel tube respectively.

FIG. 3A: Schematic perspective view of the grip of a preferred embodiment of the invention with a groove running along the upper side of the grip, the grip further having mounting brackets for mounting valves attached to or integrated into a water and/or air/suction channel.

FIG. 3B: Schematic of the routing of the channels in the embodiment of the endoscope according to the invention shown in FIG. 3A, where the water and air/suction channels branch off and bears away from the instrument channel.

FIG. 4A: Schematic perspective view of the grip of a further preferred embodiment of the invention similar to that of FIG. 3A, but with an additional mounting bracket for securing the proximal end of the instrument channel.

FIG. 4B: Schematic of the routing of the channels in the embodiment of the endoscope according to the invention shown in FIG. 4A, where the instrument channel branch off and bears away from the water and air/suction channels.

FIG. 8A: Schematic longitudinal section through the grip of a further embodiment of the endoscope according to the invention, in which the instrument channel possesses two proximal ends with openings for the insertion of an instrument.

FIG. 8B: Rear view of the embodiment of FIG. 8A (also FIG. 9).

FIG. 9: Schematic longitudinal section through the grip of the embodiment of the endoscope according to the invention shown in FIGS. 4A-4B.

FIGS. 10A-10C: An embodiment of the endoscope according to the invention with a shaft of solid material.

FIG. 11: Front view of the distal end of a further embodiment of the endoscope according to the invention with two instrument-tube-grooves.

FIGS. 12A-12B: Cross-sections through two embodiments of the tube according to the invention consisting of four sub-tubes with doubled instrument-tube.

FIGS. 14A-14B: Two views of the distal shaft end of an embodiment of the endoscope according to the invention with elastic retaining wings.

FIGS. 15A-15D: Views of the distal end of a tube according to the invention with internal partitions in embodiments with a disc-shaped thickening as a slip-back preventer compared to an embodiment without slip-back preventer.

DETAILED DESCRIPTION

Figures 5A, 5B:
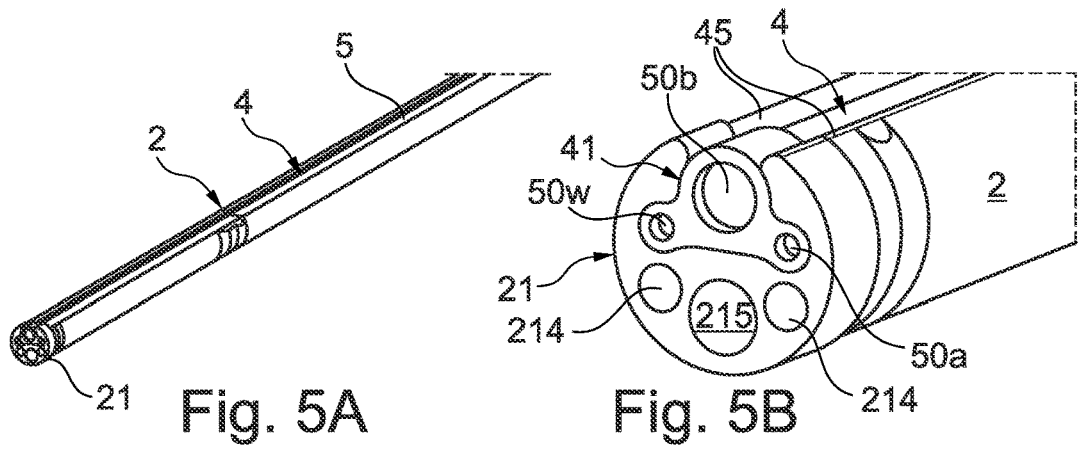
FIGS. 5A-5B: Perspective views of the shaft and its distal end of a third embodiment of the endoscope according to this invention using a three-part tube.
Figures 6A, 6B:
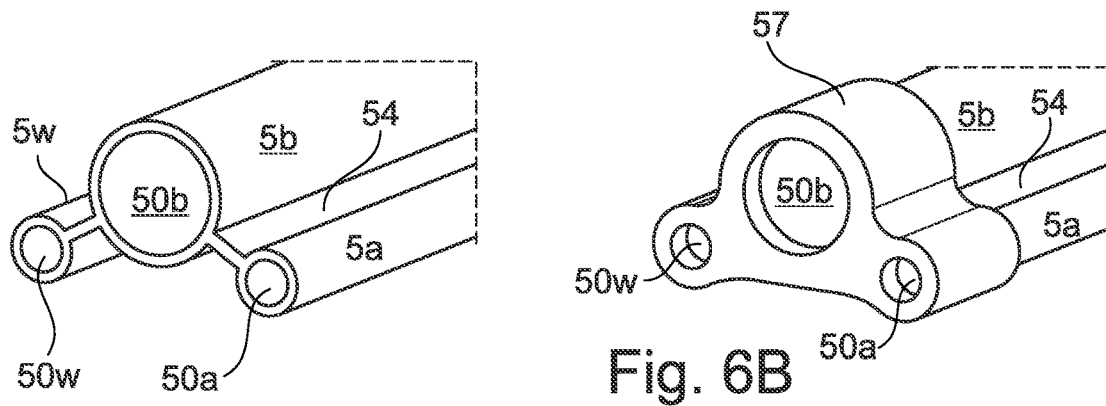
FIGS. 6A-6B: Perspective views of the distal end of a tube according to this invention consisting of three sub-tubes running parallel to and being attached to one another by thin bridges.

In the following, preferred embodiments of the endoscope of this invention will be described in detail, making reference to the figures. These embodiments are merely meant to illustrate, and not to limit the subject matter of this invention. Features may be modified and features shown in the context of different embodiments combined without departing from the spirit and scope of the invention.

In the figures, the same reference numerals are used also for different embodiments to denote features of corresponding function or meaning.

A first preferred embodiment of the endoscope of the invention is depicted in FIGS. 1A-1D, where four different views of the distal end of the shaft of that embodiment are shown.

FIG. 1A shows a head-on view of the distal end 21 of shaft 2. Visible are the distal end 41 of the groove 4 housing hollow tube 5, which in this embodiment has internal walls 52 subdividing the tube into three channels: one larger instrument channel 50b, and two smaller channels, one channel 50a, which serves to carry air or provide suction and one channel 50w carrying water. The angular alignment of the, on the outside, substantially circular tube 5 is such, that the outlet of the water channel 50w is closest to the optical lens 215 in order to be able to clean it during use of the endoscope. Given that the distal end 21 is brought into the proper position by flexing and rotation of the shaft 2, the water flowing out of the outlet of the water channel 50w may also be used to clean the lighting ports 214 arranged on either side of the line of symmetry connecting the groove 4 and the optical lens 215. Proper angular alignment of the distal end of the tube 5 is maintained by virtue of the lug 51 effectively preventing rotation of the tube 5 even when the shaft and in particular the section of it close to its distal end 21 is flexed and bent. This lug 51 can also be seen in FIGS. 1B-1D, showing perspective views of the distal end 21 of the shaft 2 of this embodiment of the invention.

The cross-sectional shape and size, of the shaft 2 and the groove 4, in particular the radial extent or depth of the groove 4, can best be seen in Subfigure A. Also shown there are the completion of the cross-section to a circle C as well as the convex hull CH. As is apparent, the center of area CoA of the circle C lies inside the groove 4 and thus the tube 5. While in the figure this can technically only be seen for the distal end, this is also the case for substantially the entire extend of the groove 4 along the shaft 2. The center of area of the convex hull CH is not shown here, but would be very close to the point CoA and also close to the groove 4 or even still contained by it. This arrangement and sizing of the groove 4 ensures that it contains a line of vanishing stretch and compression of the shaft, which has the benefit, that the axial position of any instrument inserted in the instrument channel is not or not substantially affected when the shaft 2 is bent and flexed during surgical procedures.

The groove 4 in this embodiment is, at least in the vicinity of its distal end 41, $\Omega$-shaped, to better retain the tube 5 in its seat inside the groove 4. In order not to make installing the tube overly difficult for the user or potentially damaging for the tube a moderate bulge-neck ratio of 1.3 has been chosen. However any value between 1.1 and 1.5 is equally preferred.

The groove 4 has rounded outer edges 45 in order to prevent potentially damaging the flexible tube 5 during its installation and also because a sharp edge would soon become jarred and grooved, providing a habitat for germs and microbes, reducing cleanability. For the sake of facilitating cleaning and sterilization, sharp inner edges are also avoided and the width of the groove 4 made sufficiently large to provide good access to cleaning brushes and nozzles of cleaning equipment.

While the shaft 2 and the distal end 21 in this and also the other embodiments below are shown to have a mirror symmetry, this need not be the case in general. A non-symmetric shape may also be used without departing from the spirit of this invention. However, a symmetric shape may be easier to manufacture and also more straightforward for a user of the endoscope to control and guide.

FIGS. 2A-2D illustrate the distal end of the shaft of a second preferred embodiment of the invention.

FIG. 2A shows again a head-on view while FIGS. 2B-2D show perspective views from three different angles.

In this embodiment, there are three grooves in the shaft 2: one larger groove 4 housing a tube 5b providing an instrument channel 50b and two smaller grooves 4', housing tubes 5a and 5w for providing an air/suction channel 50a and a water channel 50w respectively. All tubes have a circular cross-section. The grooves 4 and 4' have an Ω-shaped cross section to ensure proper retention of the tubes 5b, 5a and 5w after they have been installed, e.g. by plugging or pushing them into the groove lengthwise. Here a smaller bulge-neck ratio of 1.2 is shown, resulting in somewhat less but still sufficient retention and easier installation of the tubes during set-up of the endoscope before and simpler cleaning due to better accessibility of the inner walls of the grooves 4, 4' during cleaning and sterilization after use of the endoscope.

The completion shape of the shaft 2 of this embodiment is again a circle C, similar to the first embodiment of FIGS. 1A-1D. While the center of area CoA of this circle C is not contained in the main groove 4 housing the instrument channel tube 5b with the instrument channel 50b, it is still close to that main groove 4 in the sense that the point CoA lies less than half the radius of circle C from the nearest point of groove 4. Thus, the stretch/compression experienced by the groove 4 and the instrument channel tube 5b housed in it is still quite small and the undesired axial movement of an instrument inserted in the instrument channel 50b provided by instrument channel tube 5b during flexing and bending of the shaft 2 still acceptable.

As in the first embodiment, the water carried in the water channel 50w may be used to clean the optical lens 215. However, only one of the light port 214 may be cleaned easily, while the other, lying beyond the center of area CoA almost diametrically opposed to the water channel outlet 50w is harder to reach.

Also similar to the first embodiment of FIGS. 1A-1D, the outer edges 45 of groove 4 are rounded, sharp inner edges are avoided and the width of the groove 4 made sufficiently large to provide good access during cleaning and sterilization.

In FIGS. 3A-3B and FIGS. 4A-4B, the respective subfigures FIG. 3A and FIG. 4A show the grip and the proximal end of the shaft of two similar, but slightly different embodiments of the endoscope according to this invention.

Common to both is the shape of the grip 3 with control wheels 35 for controlling the direction of bend of the distal end of the shaft 2, the control wheels 35 being arranged on the right hand side of the grip 3. Also in both embodiments the groove 4 on the outside of shaft 2 is continued seamlessly on the upper side of the grip 3 right up to the proximal end 39 of the grip 3. In the groove 4, the hollow tube 5 is seated in such a way, as not to become dislodged during operations, i.e. movement involving flexing and bending of the shaft 2. Near the proximal end 39 of the grip 3 are retaining recesses 33a and 33w for mounting valves or valve blocks 53a, 53w from subfigures B by inserting them from the top into the brackets and sliding them down into a fully inserted position. The groove 4 runs straight through the mounting brackets 33a, 33w by way of slits in each of the faces of the retaining recesses facing in the axial direction.

The two embodiments shown in FIGS. 3A-3B and FIGS. 4A-4B differ only in the positioning of the open proximal end 59b of the instrument channel 50b. While in the embodiment of FIGS. 3A-3B the instrument channel extends up to the proximal end 39 of the grip 3 and thus lies behind the mounting brackets 33a, 33w for the valves, the embodiment of FIGS. 4A-4B has a retaining recesses 33b for holding the proximal end 59b of the instrument channel 50b which is positioned in direction towards the distal end of the grip 3, as seen from its proximal end 39 (cp. FIG. 4A).

This different positioning of the proximal end necessitates a different layout of the hollow tube 5 in each case which is illustrated in FIGS. 3B and 4B. As shown in FIG. 3B, in the embodiment where the proximal end 59b of the instrument channel 50b with the opening for allowing instrument insertion is positioned at the proximal end 39 of the grip 3, the water and/or air/suction channel, which before where joined with the instrument channel 50b in a multi-channel tube as shown in the cross-section and also FIG. 1, branch off from the tube 5 in a Y-junction 55 in front of the valve blocks 53a, 53w. From this point the instrument channel 50b and water and air/suction channels 50w, 50a run in separate tubes 5b, 5aw both of which are housed in the groove 4 almost up to the proximal end 39 of the grip. Y-junction 55 has a small angle between the branches connecting to tubes 5b and 5aw of 15 degrees or less in order to facilitate routing both tubes 5b and 5aw in the groove 4.

In order to enable the water and air channels to branch off from the instrument channel, they wind around the instrument duct, as can be seen from the two partial drawings of (partial) FIG. 3B. The right shows a front view of the distal end of tube 5, on which a fixing lug 51 for angular fixation in the groove is molded. The outlet openings of the water channel 50w and the air channel 50a are arranged at the bottom of the groove. In the course of the tube, the water and air ducts wind around the instrument duct so that they are in the area of the junction 55 above the instrument duct come to rest, as in the partial drawing on the left, which shows a cross-section through the tube in the area in front of the junction 55 can be seen. The twist angle between the distal end of the tube and junction 55 is approx. 120 degrees, whereby a twist angle between 0 and 180 is generally possible, but angles between 30 and 150 degrees, in particular 60 and 120 degrees, are preferred.

In the embodiment of FIGS. 4A-4B, where the proximal end of the instrument channel 50b with its insertion opening lies in front of, i.e. towards the distal end 31 of the grip 3, the instrument channel 50b branches off as a separate tube 5b in Y-junction 56 having a significantly larger angle of about 30 degrees, in order to facilitate access to the insertion opening, when the proximal end 59b is inserted in mounting bracket 33b.

In both embodiments the proximal end 59b of the instrument channel tube 5b comes with a fixing structure which serves to simplify handling and securing of the proximal end 59b by inserting the fixing structure in an appropriately shaped mounting bracket (mounting bracket 33b in FIG. 4A, not shown in FIG. 3A). The two shapes of the fixing structure shown here, a disc-like fixing structure 53b in FIG. 3B and oblong fixing structure 53b' with square cross-section in FIG. 4B are just two of many possible variants all of which may be realized within the scope of this invention.

The main advantage of the embodiment from FIGS. 3A-3B is that the instrument channel 50b runs straight along the entire endoscope from end to end without any sharp bend, keeping friction of an instrument wire inserted in the instrument channel 50b low and thus facilitating insertion and movement and precise positioning of instruments. While in the embodiment from FIG. 4, the Y-junction 56 does introduce a sharper bend which increases friction forces, it has the advantage of making the instrument channel 50b shorter overall, which somewhat offsets the increased friction from the bend and, moreover, places the proximal end more ergonomically as the position of the mounting bracket 33b is easier to reach during insertion of an instrument (wire) by a user holding the endoscope than the proximal end 39 of the grip 3, where the insertion opening of instrument channel 50b is placed in the embodiment of FIGS. 3A-3B.

FIGS. 5A-5B, FIGS. 6A-6B and FIGS. 7A-7C depict a third preferred embodiment of an endoscope according to this invention. FIG. 5A shows the shaft 2 and FIG. 5B a close-up view of its distal end 21.

As can best be seen from FIG. 5B the groove 4 in this embodiment is neither U- nor omega-shaped cross-section as in the other embodiments, but is roughly T-shaped, matching the cross-section of the tube 5, which in this embodiment consists of three sub-tubes 5b', 5a' and 5w' each providing one working channel. The largest sub-tube, 5b', serves to form the instrument channel 50b, the two smaller ones serve as water and air/suction channels 50w and 50a respectively. The three sub-tubes 5b', 5a' and 5w', being arranged in a mirror symmetric triangular pattern, run parallel to and at a distance from each other, the two smaller diameter sub-tubes 5a' and 5w' being connected to the larger sub-tube 5b' by thin bridges 54 of the same material as the tubes themselves.

As shown in FIG. 5B, the distal end of the tube 5 is securely held in the recess formed by the distal end 41 of the groove 4 in the distal end 21 of the shaft 2 by an end cap 57, which is pushed over the distal end of the tube 5 before installation of the tube 5 in the groove 4. The groove 4 has along its entire extent a width big enough to allow easy access for cleaning and sterilization purposes. To facilitate these preparation activities further, as in the other two embodiments, sharp inner edges are avoided and the outer edges 45 are rounded. The latter also helps to protect the multi-part hollow tube 5 from being accidentally cut or ruptured during installation.

In this embodiment too the shaft 2 has a cross-section that is, apart from the groove, circular, or, more precisely the completion—as defined above—of the cross-section is a circle. A circle is generally the preferred shape for cross-sections of endoscope shafts as it maximizes the area for a given circumference, thus minimizing patient discomfort and pain caused by the insertion of the endoscope. The groove has a depth extending right up to the center of area of the cross-section of the shaft, or rather its completion.

Due to the shaping of the multi-part tube 5, its installation in groove 4 can in only with difficulty and only with large deformation of the tube 5 be effected by placing the tube parallel to an on top of the groove and then pushing it into its seat in the groove by application of force in the radial direction, proceeding in sections lengthwise along the shaft, as was the simplest and quickest, and thus recommended, installation method in the case of the other two embodiments of FIGS. 1A-1D and 2A-2D. Instead, the tube 5 of this embodiment is best pushed into groove axially from the distal end. To facilitate this, its cross-sectional size is chosen smaller than that of the groove 4 in order to leave a clearance, because otherwise friction between the outside surface of the tube 5 and the walls of groove 4 would prevent quick and simple installation. Since due to this clearance a secure seat of the distal end of tube 5 in the recess is no longer guaranteed, end cap 53*b* is provided.

Figures 7A, 7B, 7C:
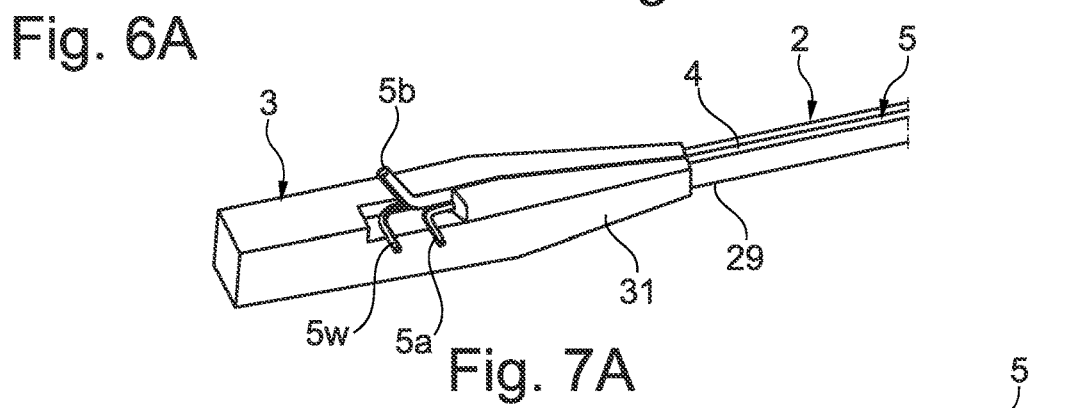
FIGS. 7A-7C: Perspective views of the proximal end of the shaft and the distal end of the grip of an embodiment of the endoscope according to this invention using the three-part tube shown in FIG. 6 showing the branching-off point of the instrument and water and air/suction channels.

FIG. 7A and close-up FIGS. 7B-7C show the proximal end 29 of the shaft 2 which is attached to the distal end 31 of the grip 3. The advantage of this three-part layout of the tube 5 becomes apparent when regarding FIGS. 7A-7C: since the sub-tubes 5*a*' and 5*w*' can easily be separated from tube 5*b*' at any desired point, there is no need for providing any Y-junction of a certain exact angle at exactly the right distance from the distal end of tube 5. Instead, the thin bridges 54 connecting the sub-tubes can be cut and the sub-tubes simply pulled apart at the desired point, for instance inside a separation zone 37 in the form of a recess in the grip 3 which the present embodiment provides for this purpose, and secured at or attached to their respective appropriate fixation/attachment point: the instrument channel tube 5*b*' is secured to the grip, e.g. in a mounting brackets as in FIGS. 3A-3B and FIGS. 4A-4B, and the water and air/suction channel tubes 5*w*', 5*a*' are attached to valves on the grip or some other source of controlled water or air flow.

FIGS. 8A-8B show a schematic longitudinal section through the grip of a further embodiment of the endoscope according to the invention, which combines the elements of the embodiments from FIGS. 3A-3B and FIGS. 4A-4B and also illustrates the exact course of the individual tubes inside the grip.

The groove according to the invention, not shown here, is also continued seamlessly in the grip 3 in this embodiment. It runs directly above optical fibers or electrical cables 36 which lead through the grip 3 and the shaft 2 to the optical elements (lens, light outputs or camera chip and LED) in the distal end of the shaft. The tube 5 inserted in the groove comprises a combined instrumentation and suction channel 50*b*, a water channel 50*w* and an air channel 50*a*. The course of the instrument channel 50*b* branches several times: a first Y-shaped branch 56 is located in the area of the distal end 31 of the grip 3. The branch 5*b*1 branching off there leads to a first proximal end 59*b*1 detachably fixed in a first holding structure 33*b*1 on the upper side of the grip, wherein this branch branches off at a relatively large angle of approximately 30 degrees to the course of the tube 5. The second branch 5*b*2 of the combined suction and instrumentation channel continues in the groove up to a junction 55, in which the instrumentation channel 50*b* again splits up into a third and fourth branch, the third branch 5*b*3 leading to a second proximal end 59*b*2, which is detachably fixed in a holder 33*b*2 in the proximal end 39 of the grip 3. The fourth branch 5*b*4 of the instrument channel is led together with the air channel 50*a* and the water channel 50*w* to valves in valve blocks 53*aw*, 53*s* which are provided in holders 33*aw* and 33*s* in the upper side of the grip 3. By means of the valve 53*b*, for the purpose of generating suction there may be controllably created a low pressure in the instrument channel 50*b*, for which the proximal end 5, not shown, of the fourth branch 5*b*4 must be connected to a vacuum source. Likewise, the open ends of the water channel 50*w* and the air channel 50*a* emanating from the combined valve 50*aw* for the control of the water rinsing and air insufflation respectively have to be connected to corresponding sources of water and compressed air. As can be seen in the right part of FIG. 8A, the suction, water and air channels are continued after the valves 53*aw*, 53*b* in a widening of the downwardly bending groove 4 in the proximal end 39 of the grip 3 as independent sub-tubes 5*b*4, 5*a* and 5*w*, which means that they restrict the movement of the endoscope and the activity of its user as little as possible. The size and course of the groove 4 in the proximal end 39 of the grip are also shown in the schematic rear view of the endoscope in FIG. 8B.

In FIG. 9 is shown in more detail the course of the tubes or channels in the grip of the embodiment of the endoscope according to the invention of FIGS. 4A-4B. It largely corresponds to that of the embodiment from FIGS. 8A-8B, with the difference that there is no second branch in the instrumentation tube, and thus the second branch 5*b*2 of the instrumentation tube 5*b* continued in the groove 4 after the first branch 56 together with the supply tubes for water 5*w* and (compressed) air 5*a* is guided directly to the valve blocks in the holders on the top of the grip 3, more precisely in the case of the second branch of the instrumentation tube 5*b*2 to the suction valve 53*s*. The rear view of the endoscope grip from FIG. 8B can also be transferred to the embodiment of FIG. 9.

FIGS. 10A-10C show an embodiment of the endoscope according to the invention with a solid shaft.

The upper part of FIG. 10A shows the shaft 2 with the deep groove 4, which is characteristic of the present invention, on the outside of and ending in the recess 41 of the distal end of the shaft 2, which also houses the optical observation means 215 and the illumination means 214.

The lower part of FIG. 10A shows a cross section in the cut surface indicated above. As shown, the shaft 2 is made of a solid material, in which the hydraulic lines 37 and a channel with control lines 36 for controlling the optical or lighting components 214, 215 are embedded. The solid material is preferably sufficiently stiff to enable good positioning of the endoscope tip 21 even against the resistance of the patient's tissue, but at the same time flexible enough to rule out tissue damage to the patient.

FIG. 10B shows an embodiment of a grip 3 of an endoscope with a solid shaft and hydraulic control as in FIG. 10A. The groove 4, Haltestruk15, continued over the entire length of the grip 3 retaining structure 33*b* near the distal end of the grip 31, suction valve block 53*s*, combined water and air valve block 53*aw*, instrument opening 59*b* and sub-tubes 5*b*, 5*a* and 5*w* are known from the embodiments in FIGS. 4A-4B and FIG. 9, respectively. The difference in the present embodiment is that instead of control wheels, toggle or rocker switches 38 are used to control the bending of the shaft 2. The endoscope operator can use the rocker switch 38 to control the pressure applied to the hydraulic lines 37. A bend in the shaft 2 results from a pressure difference between the hydraulic lines 37.

FIG. 11 shows a front view of the endoscope tip of an embodiment of the endoscope according to the invention, in which the shaft has two grooves for receiving an instrument tube.

Similar to the embodiments of FIGS. 1A-1D and FIGS. 2A-2D, the distal end 21 of the endoscope shaft has a centrally arranged optic 215 with two laterally arranged light outputs 214. In a line with the light outputs 214 are two U-shaped grooves 4' of smaller diameter for receiving one each water and (compressed air tube) available. In mirror symmetry above and below the plane defined by the grooves 4', Ω-shaped grooves 4 are arranged, which are each sufficiently large to be able to receive instrument tubes. As a result, two instruments can be used at the same time in an endoscope according to this embodiment. It is therefore possible to work with both hands, which can mean a simplification or acceleration in some examinations or operations. In order, despite the two comparatively deep grooves 4, to still have sufficient space for the control of the optics 215 and the light outputs 214 as well as the Bowden cables or hydraulic lines that enable the shaft to move, the shaft in this embodiment has a slightly elliptical outline or a slightly elliptical completion C, wherein the large semi-major axis pointing in the direction of the deep grooves.

A similar aim is pursued by the embodiments shown in FIGS. 12A-12B of a tube consisting of several sub-tubes. In both variants according to FIG. 12A and FIG. 12B, the tube 5 consists of four sub-tubes, namely two smaller supply tubes 5a', 5w' and two larger working tubes 5b.

In FIG. 12A, the sub-tubes are arranged approximately in the form of an inverted "T", with the two working or instrument tubes 5b', which provide channels 50b for instruments or for suction, running centrally one above the other and over a thin bridge 54 are connected to each other. The smaller tubes 5a' and 5w' with an air channel 50a or water channel 50w run to the side of the lower sub-tube 5b' and are connected to this via material bridges 54.

In FIG. 12B, the two work or instrument tubes 5b, which provide channels 50b for instruments or for suction, are arranged next to one another. A smaller supply tube connects to both of them laterally offset downwards and connected via bridges 54: on the left an air tube 5a' with the air duct 50a and on the right the water tube 5w' with the water duct 50w. When used in an endoscope with a complementary shaped groove, both embodiments of the tube allow the simultaneous use of two instruments.

In the embodiments of the endoscope according to the invention with a double instrument tube, two proximal accesses are accordingly also necessary in order to be able to insert the instruments into the respective channels independently of one another. These accesses can either both be provided in the distal area of the grip or both 5 at the proximal end of the grip and fixed in corresponding holding structures. Alternatively, as shown in FIGS. 8A-8B, one access can be fixed distally on the grip and the other proximally on the grip, that is, the embodiments of the endoscope shaft according to FIG. 11 can be combined with the embodiment of the grip according to FIGS. 8A-8B.

Figure 13:
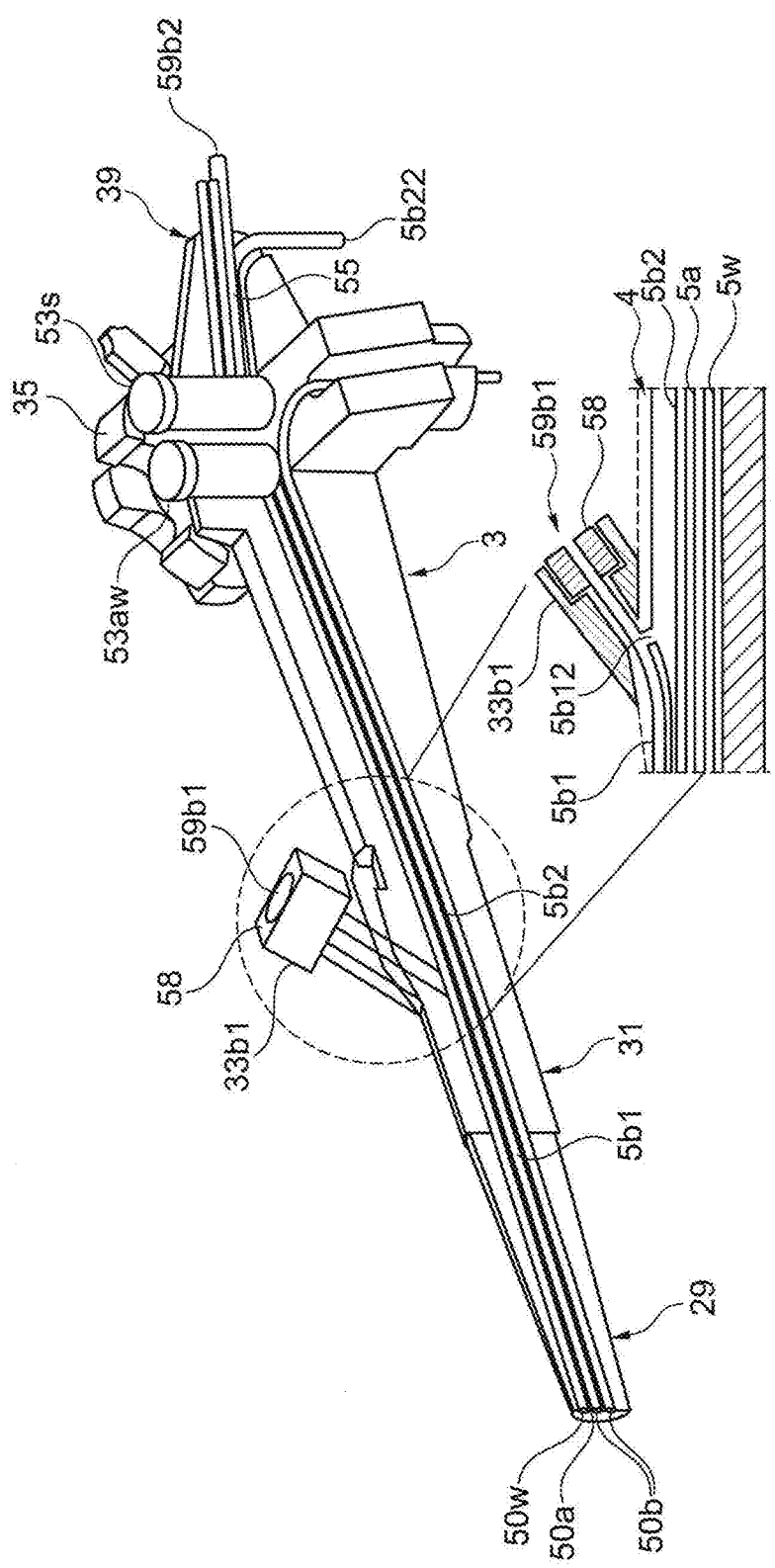
FIG. 13: Embodiment of the endoscope according to the invention with two instrument channels, whereby the access opening of one is positioned distally, that of the other proximally in the grip.

Even in the present embodiment with a double-barreled instrument channel, it is basically sufficient to continue to provide only a single suction valve, that is to say to use only one of the instrument channels as a suction channel. However, in order to prevent the channel that is not set up for suction, which is usually the one of which access opening is fixed distally in the grip, from being clogged with impurities when an instrument such as biopsy forceps is repeatedly passed through, which when the pressure increases at the surgical site could well spill out of the access opening and contaminate the outside of the endoscope, it is proposed that the two instrumentation channels be placed in fluid communication with one another via an open, short-distance connection. This connection is preferably provided in the area of the grip, as proximally as possible. By establishing such an open connection it is achieved that the second biopsy channel is also automatically sucked off, so to speak, and thus kept free of contamination. A variant of the endoscope according to the invention with a double-barreled instrument channel is shown in FIG. 13.

The figure shows the grip 3 with the top-side groove 4 in which the exchangeable tube 5, consisting of four sub-tubes, a first instrument tube 5b1, a second instrument tube 5b2, a compressed air tube 5a and a water tube 5w, runs. The proximal end of the first instrument tube 5b1 with the access opening 59b1 is fixed in the holder 33b1 in the distal region 31 of the grip 3. The second instrument tube 5b2, which is also used for suction, is guided in the groove 4 over the suction valve 53s to the proximal end of the grip, where the access opening 59b2 to the second instrument tube is fixed. A branch 5b22 of the second instrument tube continues from junction 55 to a connection to a vacuum source. The water and air tube 5w and 5a run via the combination valve 53aw to the proximal end 39 of the grip 3, where they leave the groove 4 and the endoscope 1 and continue to the respective connections.

The lower partial drawing shows an enlarged section of the distal grip end 31 with the holding structure 33b1 above the groove 4 for fixing the fixing structure 58 of the proximal end of the first instrument channel 5b1 with access opening 59b1. A short open connection 5s12 ensures fluid communication between the two instrumentation channels 5b1 and 5b2, so that the first instrumentation channel 5b1, which is not directly connected to the suction valve, is also sucked off and remains free of contamination.

What is shown is an endoscope equipped with control wheels 35, but the type of control is largely independent of the design of the groove and the tubes and is also compatible with, for example, a hydraulic control.

FIGS. 14A-14B are two views of an embodiment of the endoscope according to the invention, in which the tube is held in the groove at least in the region of the distal end of the shaft by means of elastic retaining wings. FIG. 14A shows a front view without a tube, but FIG. 14B shows an elevated perspective view with the tube 5 inserted into the groove 4.

The retaining wings 49 protrude into the neck of the shaped groove 4. As indicated by the arrows, the retaining wings 49 are elastic, for example made of rubber, and can thus give way when the tube is inserted into and removed from the groove 4. As can be seen in part B, the retaining wings 49 are arranged axially offset. The foremost retaining wing 49 is attached shortly behind the cap that forms the distal end of the shaft 2.

The distal end of the tube 5 is prevented from rotating relative to the groove by the fixing lug 51, primarily in order to fix the relative alignment of the water channel to the optics 215 and the lighting 214.

FIGS. 15A-15B show two views of an embodiment of the flexible tube 5 according to the invention, which has a bead-like, annular thickening which forms a slip-back prevention against sliding back of the shaft end when the length of the groove in the endoscope shaft changes when the shaft is bent. In comparison, FIGS. 15C-15D show a tube without anti-slip preventer.

The annular thickening 51' is integral with the distal end of the tube 5, and consists of the same material as the rest of the tube including the partition walls 52, which, in the manner already described above, divide the tube interior into three parallel channels, a working channel 50b and a water channel 50w and divide an air insufflation channel 50a.

Figures 15E, 15F:
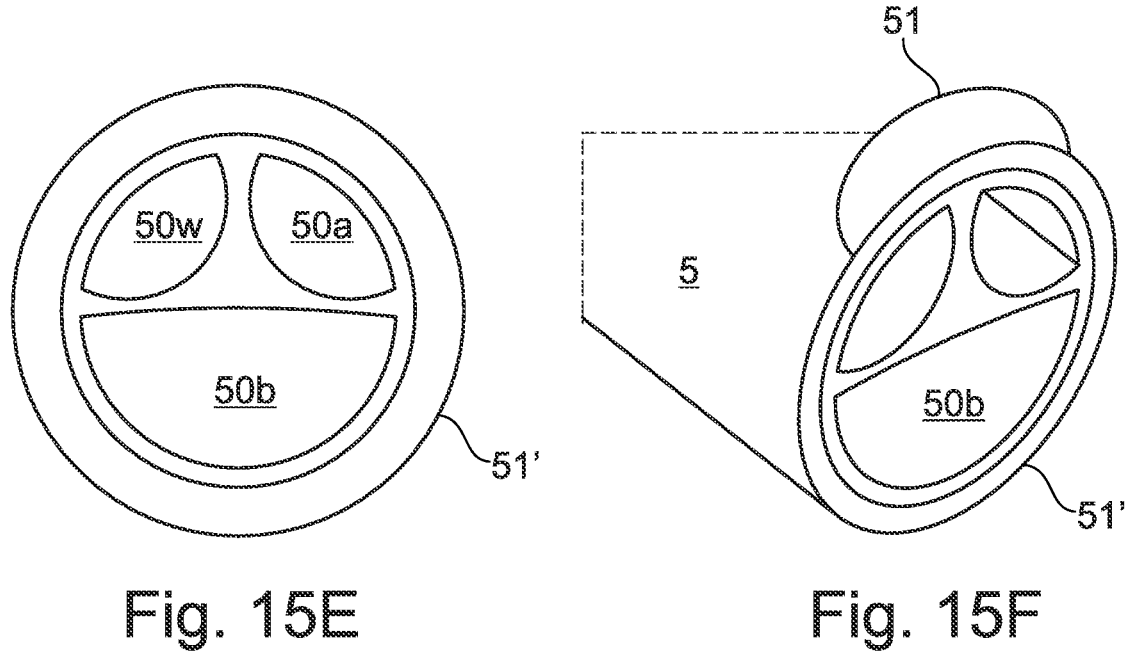
FIGS. 15E-15F: Two views of the distal end of a tube according to the invention with internal partitions in embodiments with a plastic disc as a slip-back preventer in combination with a fixing lug.

In FIGS. 15E-15F, an embodiment of the distal end of the tube is shown in which the anti-slip device is formed by an annular plastic disc which is attached, for example glued or welded, to the distal end of the tube 5. In addition, an elevation 52 made of the same plastic material is also integrated into the disk 51', which serves as a fixing lug 52.

Figure 16:
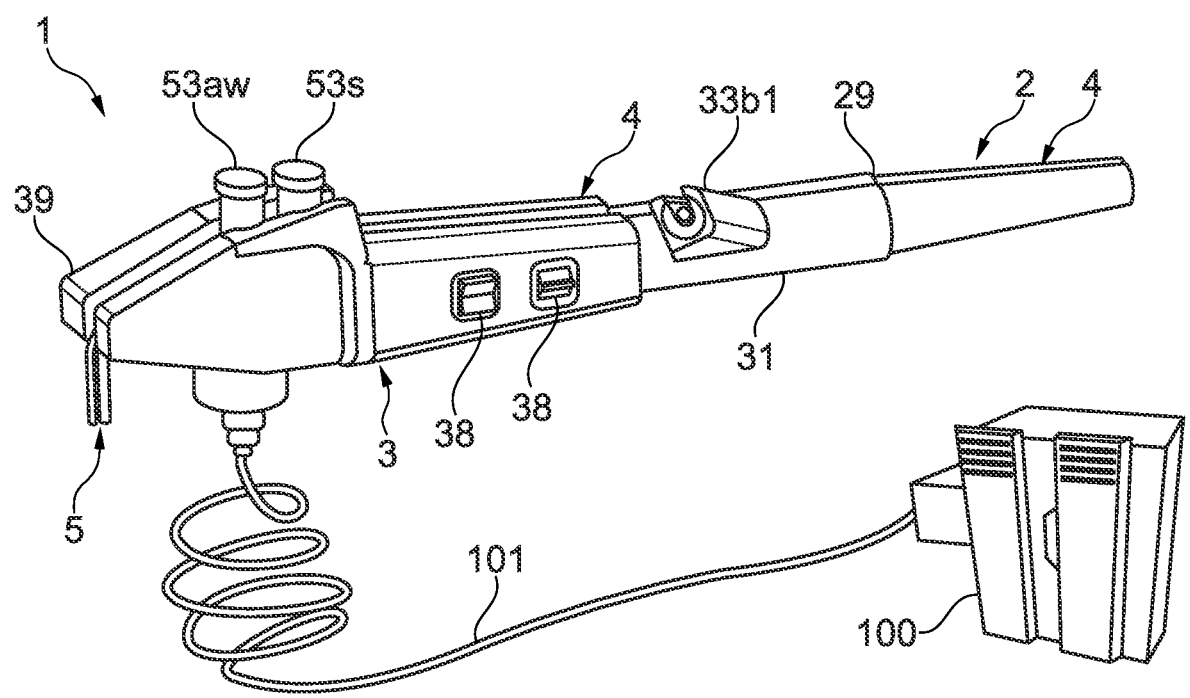
FIG. 16: Perspective view of a hydraulically actuated embodiment of the endoscope according to the invention.

FIG. 16 shows a further perspective view of the hydraulically actuated embodiment of the endoscope according to the invention of FIG. 10B. The endoscope 1 has a shaft 2 which merges via a proximal shaft end 29 into the distal end 31 of the grip part 3. In the area of the distal end of the grip part 31, a fixing structure 33b1 for a biopsy access is formed. The groove 4, in which, according to the invention, the tube 5 comprising a plurality of working channels is inserted, there being at least one free section in which the tube has play in the groove so that it can move slightly axially relative to the groove walls but can also twist tangentially, runs from the (not visible) distal end of the shaft on the upper side through the entire shaft 2, continues in the grip part 3 and leads there to the proximal end of the grip 39. Grip end 39 led downwards. Suction, water and air (sub) tubes are led downwards via a groove in the rear end of the grip 39.

Integral valve blocks 53aw with an air valve and a water valve 53 and with a suction valve are incorporated into the tube 5 and are inserted into complementary holders on the upper side 5 of the endoscope.

To control the bending of the shaft 2, two rocker switches 38 are arranged on the side of the grip, with which a user can control the bending of the shaft 2 in the left-right direction and the other in the vertical up-down direction. The hydraulic system integrated in the grip 3 is supplied with electrical energy from the processor 100 via the connecting cable 101.

The great advantage of this embodiment is its easy handling. Up to now it has been customary to provide endoscopes with a supply cord in which the comparatively stiff water, air and suction channels emerging from the endoscope shaft were combined. These were not designed as removable, disposable tubes as here, but permanently connected to the device. The stiff supply cord made the use of conventional endoscopes very unwieldy. Since presently only one flexible connection cable 101 is connected to the power supply unit 100, and the tubes 5, which are routed separately at the proximal end of the grip from the endoscope 1 to the respective supply units, are flexible.

Since the rocker switches 38 replace the usual rotary wheels here, surface disinfection of the endoscope grip is also significantly simplified.

Figure 17A:
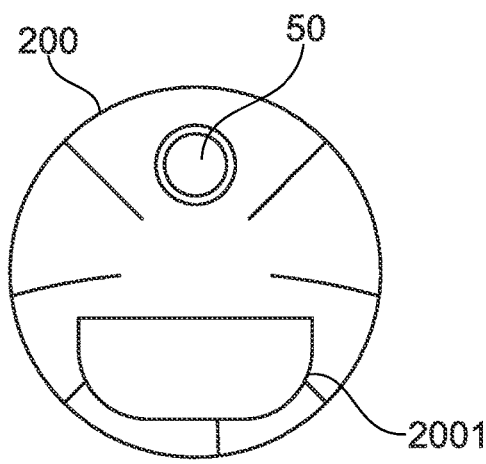
FIG. 17A: Front view of a contamination protection cover with an integrated tube for use with an endoscope according to the invention.
Figure 17C:
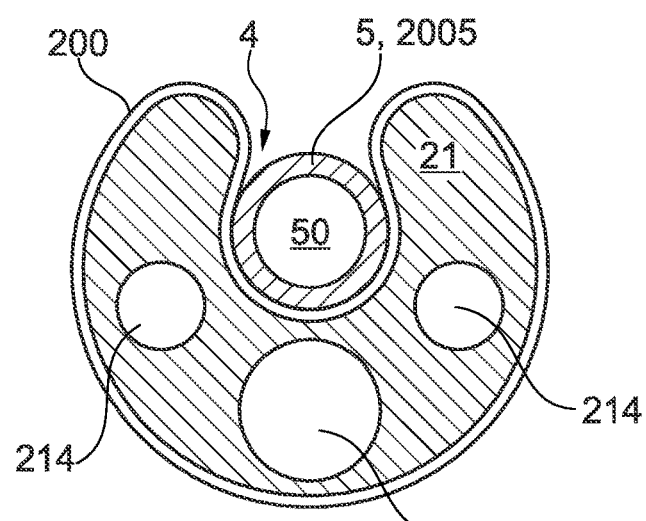
FIG. 17C: Cross-section through the distal shaft end of a preferred embodiment of the endoscope according to the invention over which the cover of FIGS. 17A and 17B is drawn.
Figure 17B:
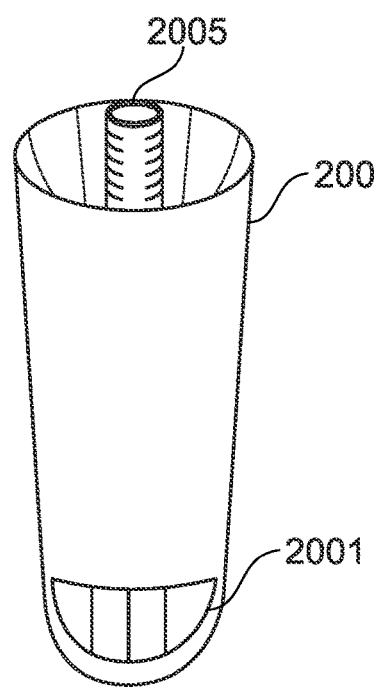
FIG. 17B: Cut-open perspective view of the cover of FIG. 17A.

FIGS. 17A-17C represent a further preferred embodiment of the endoscope according to the invention, in which the tube inserted into the groove is integrated into a contamination protection sleeve made of a highly elastic material and tightly enclosing the endoscope shaft.

FIGS. 17A-17B show the protective sheath 200 without the endoscope shaft. FIG. 17A shows a front view and FIG. 17B shows a cut-open perspective view of the protective cover 200. As shown, the integrated tube 2005 opens into an opening 50 in the upper area. In a lower area, a transparent window 2001 is provided, which, after the cover has been pulled onto the endoscope shaft and the integrated tube 2005 has been clicked into the groove 4 in the endoscope shaft, coincides with the endoscope optics in the form of the lens 215 and the lights 2014 in the tip 21 of the shaft 2, so that the use of the optics is not hindered by the sheath 200. Instead of the shape shown, the window 2001 can also be made larger. For example, the entire tip of the sheath 200 can be made transparent.

In the figures, a single-lumen tube is shown for the sake of simplicity, but in alternative designs a multi-lumen tube, either a tube with an approximately round or elliptical cross-section and internal dividing walls, or a tube with round or elliptical sub-tubes connected by thin bridges, can be used.

The shape of the sleeve 200 shown in. 17B corresponds to the shape which it attains by pulling it onto the shaft 2 and not to the shape before pulling it on. In the latter, the sheath 200 is, in order to save space, preferably rolled up to its cap-like tip to form a torus. To place it on the shaft, the cap would first be pushed onto the shaft tip 21 and the sheath 200 then rolled over the shaft like a condom, the tube 2005 integrated in the sheath 200 being pressed or pressed into the groove 4 in the shaft 2.

The state then reached is illustrated in FIG. 17C, which shows a cross section through the shaft tip 21 with the sheath attached.

Figure 18:
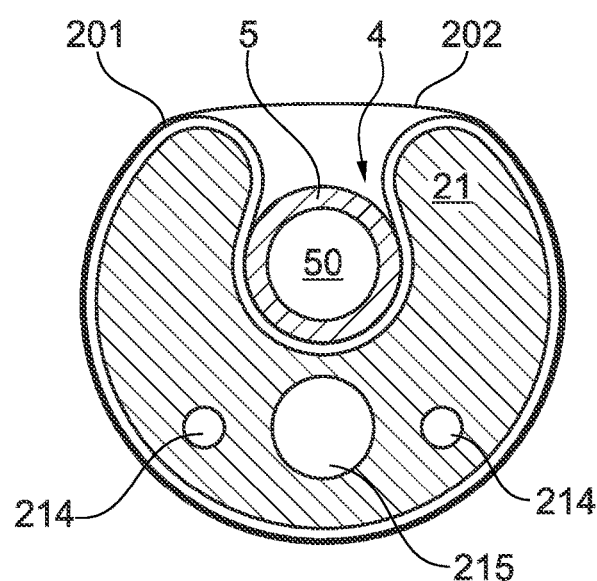
FIG. 18: Cross-section through the distal shaft end of the preferred embodiment of the endoscope according to the invention of FIG. 17C, however, with two covers drawn over the shaft one on top of the other and a separate tube sandwiched between the covers and inserted into the groove of the shaft.

Similar to FIG. 17C, FIG. 18 shows a cross-section through a shaft tip of an endoscope according to the invention, however, here two sleeves are used, which, outside of the groove 4, closely conform to the outer surface of the shaft 2 due to their inherent elasticity. In case of the inner sleeve 201 this, however, also holds inside the groove 4, whereby it is here pressed more or less strongly against the inner walls of the groove 4 by the tube 5 that is seated in the groove 4. In the free sections of the tube according to the invention, in which it may easily move relative to the groove, the clamping pressure is lower to not present at all, in the sections of the tube outside of the free sections, in which the tube 5 is firmly held in the groove 5, it is higher. The outer sleeve 202 surrounds the inner sleeve 201 and the tube. Since it is not being pressed into the groove by the tube 5, the cross sectional shape it attains due to its elasticity corresponds nearly exactly to the mathematical convex hull of the shaft cross section.

LIST OF REFERENCE SIGNS 1 endoscope
2 shaft
21 distal end of shaft 2
214 light port
215 optical lens
29 proximal end of shaft 2
3 grip
31 distal end of the grip 3
33b retaining recess for fixing structure
33b1 first (distal) retaining for fixing structure 58
33b2 second (proxima) retaining for fixing structure 58'
33a, 33w retaining recess for valve blocks
35 control wheels
36 optical fibers/electric cables
37 hydraulic line
38 rocker switch
39 proximal end of the grip 3
4 main groove
4' additional grooves
41, 41' distal end of the grooves 4, 4'

45, 45' outer edges of grooves 4, 4'
49 retaining wing
5 working channel tube
5b, 5b' instrument channel tube
5b1 first (branch of the) instrument channel tube(s)
5b2 second (branch of the) instrument channel tube(s)
5b22 branch of the second instrument channel tube
5b3 third branch of the instrument channel tube
5b4 fourth branch of the instrument channel tube
5a, 5a' air/suction channel tube
5w, 5w' water channel tube
5s12 open connection
50 channel in the interior of 5
50b instrument channel (outlet)
50a air/suction channel (outlet)
50w water channel (outlet)
51 fixing lug
51' slip-back prevention disc
52 subdividing walls
53b, 53b' fixing structure
53a, 53w valve blocks air/suction and water
53s valve block suction
54 bridges connecting sub tubes
55 shallow angled Y-junction
56 steeper angled Y-junction
57 end cap of multi-part tube
58, 58' fixing structure
59b proximal end of instrument channel
59b1 first proximal end of the instrument channel
59b2 second proximal end of the instrument channel
100 processor
101 connection cable
200 sleeve
2001 window in 200
2005 tube, integrated in 200
201 inner sleeve
202 outer sleeve
C completion of shaft cross-section
CH convex hull of shaft cross section
CoA center of area of completion

The invention claimed is:

1. An endoscope for the minimal invasive examination or surgical treatment of a patient, the endoscope comprising:
a flexible tubular shaft for insertion into the patient, the shaft having a proximal end, a distal end, and at least one groove extending axially along an outer face of the shaft from a vicinity of the proximal end and ending in a recess in the distal end;
a grip for holding the endoscope, the grip having a distal end attached to the proximal end of the shaft; and
at least one hollow tube removably housed in the groove of the shaft, the tube comprising at least one working channel for internally guiding a surgical instrument and/or carrying water or air to or providing suction at the distal end of the shaft;
wherein a convex hull or a completion of the shaft without the hollow tube is the same as a convex hull or completion of the shaft with the hollow tube;
wherein the groove of the shaft and the tube are dimensioned relative to one another such that at least one free section of the tube housed in the groove of the shaft has, in the straight extended state of the shaft, an exterior cross-section which is smaller than an interior cross-section of the groove; and
wherein the at least one free section of the tube has a higher deformability by being shaped in a bellows-like or spiral tube-like manner, and/or by being made of a material of higher elasticity, and/or by having a lower wall thickness.

2. The endoscope according to claim 1, wherein the at least one free section of the tube comprises two or more free sections connected by other sections of the tube which are equal in length and have a lower deformability than the free sections, the other sections of the tube being firmly retained in the groove by means of complementary sizing or a low-strength adhesive.

3. The endoscope according to claim 1, wherein:
the at least one free section extends over the entire length of the shaft and the entire length of the groove, the tube having an exterior diameter which is, at least in a straight extended state of the shaft, smaller than an interior diameter of the groove, and
during bending of the shaft, the hollow tube is secured against slipping out of the groove by means of two or more elastic retaining wings, and/or is secured against sliding back into the groove at the distal end by a slip-back-preventer in the form of an annular disc located at a distal end of the tube and inserted into the distal end of the groove.

4. The endoscope according to claim 1, wherein the groove:
has rounded edges, and/or
extends over the entire length of the shaft from the distal end to the proximal end and extends to an upper surface of the grip, and/or
has a cross-section which is U- or Ω-shaped and constant along the shaft, and/or
runs spirally around the shaft, where the spiral course covers an angle of between 0° and 180° and preferably between 30° and 150°, and/or
has a cross section which is U- and/or Ω-shaped and not constant along the shaft, where the groove: varies in shape between a U- and an Ω-shape; and/or varies in cross-sectional area, where in particular a locally minimal cross sectional area and/or a Ω-shape of the groove is attained at or near the distal end; and/or has at the proximal end of the shaft and/or in the grip an enlarged cross section for the purpose of enabling insertion of valves that are integrated into the tube and inserted into valve mounts of the grip.

5. The endoscope according to claim 1, wherein the grip has at least one holder:
for receiving a valve of a water channel or a valve of an air/suction channel, in particular one or multiple recesses in the grip, whereby the valves are integrated into valve blocks that are unitary with the tube for facilitating their insertion into the holder, and/or
for fixing a proximal end of an instrument channel of the tube, where the proximal end of the instrument channel has a fixing structure for facilitating its insertion into the holder.

6. The endoscope according to claim 1, wherein:
the shaft has a symmetric cross-section, preferably a circular, elliptical or oval cross-section, and the groove lies in a plane of symmetry of the shaft, and/or
the shaft is made from a solid material, in particular a plastic, and/or
the at least one groove comprises two grooves suitable for receiving an instrument tube.

7. The endoscope according to claim 1, wherein the groove contains along its entire extent a center of area of a convex hull or a completion of a cross-section of the shaft.

8. The endoscope according to claim 1, wherein the tube:
has a cross-section which is complementary to a cross-section of the groove, and
is made from an elastic material and has a diameter that is larger than a diameter of the groove at least at two points along the shaft, one of these points lying at or near the distal end, the tube thereby being fastened in the groove due to elastic forces.

9. The endoscope according to claim 1, wherein the tube:
is made of a flexible material in the form of rubber or a soft plastic and has an open distal end and at least one open proximal end, the at least one working channel comprising more than one working channel provided in an interior space of the tube and serving as a suction channel for providing suction or a channel for carrying water or air; and
has internal walls subdividing the interior space of the tube into at least two separate working channels, or is formed of two or more subtubes spaced apart from and running parallel to each other, which are connected to each other by, in comparison to a diameter of the subtubes, thin bridges comprised of a wall material of the subtubes.

10. The endoscope according to claim 9, wherein the working channels of the tube comprise three axial channels, one of the axial channels having a cross-sectional area larger than the other two axial channels and being configured for guiding a surgical instrument, and the other two axial channels of a cross-sectional area smaller than the one axial channel being configured for carrying water and air or providing suction.

11. The endoscope according to 10, wherein a radial fixing lug is provided at the distal end of the tube for ensuring that outlets of the other two axial channels maintain a proper angular alignment relative to an optical lens in the distal end of the shaft.

12. The endoscope according to claim 10, wherein the three axial channels wind spirally around each other with a winding angle of between 0 and 180 degrees, preferably between 30 and 150 degrees.

13. The endoscope according to claim 10, wherein the tube has a Y-junction where the one of the axial channels, which continues in a separate instrument channel tube, branches away from the other two axial channels, which jointly continue in a separate water and air/suction channel tube, and at least one of the separate instrument channel tube and/or the separate water and air/suction channel tube are housed in the groove.

14. The endoscope according to claim 13, wherein:
a proximal end of the instrument channel tube has a fixing structure preferably made from the same material as the tube, and/or
the air/suction channel and the water channels each have a valve or share a common valve, and/or
the instrument channel tube has a valve such that the instrument channel may serve as suction channel, whereby the valves are in particular each integrated into valve blocks that are unitary with the respective tube, and/or
the tube comprises two working tubes which are in fluid communication with each other via an open connection, and/or
the tube is integrated into a contamination protection sleeve that can be pulled over the shaft.

15. The endoscope according to claim 9, wherein the tube has an annular disc as a slip-back-preventer for preventing the tube from sliding into the groove.

16. The endoscope according to claim 1, wherein the tube:
is made of flexible material in the form of rubber or a soft plastic and has an open distal end and at least one open proximal end, the at least one working channel comprising more than one working channels provided in an interior space of the tube and serving as a suction channel for providing suction or a channel for carrying water or air; and
comprises a plurality of subtubes disposed at a distance from and running parallel to each other, the subtubes being connected to each other by bridges made of a wall material of the subtubes, said bridges having a thickness that is small in comparison to a diameter of the subtubes.

17. The endoscope according to claim 16, wherein the plurality of subtubes comprise a water-channel-subtube, an air-channel-subtube, and one or two instrument-channel-subtubes.

18. The endoscope according to claim 1, wherein the tube:
is fixed inside the groove with a glue of low adhesive strength, and
is integrated into a highly elastic contamination protection sleeve that can be pulled over the shaft.

19. The endoscope according to claim 1, wherein the exterior cross-section of the at least one free section of the tube is smaller than the interior cross-section of the groove to permit the tube to undergo both axial movement relative to inner walls of the groove and rotational movement relative to a longitudinal axis of the groove.

* * * * *